(12) United States Patent
McMahon et al.

(10) Patent No.: US 10,945,594 B2
(45) Date of Patent: Mar. 16, 2021

(54) VAGINAL SPECULUM WITH ILLUMINATOR

(71) Applicant: Welch Allyn, Inc., Skaneateles, NY (US)

(72) Inventors: Michael T. McMahon, Syracuse, NY (US); Robert L. Vivenzio, Auburn, NY (US); Roger P. Bonenfant, Victor, NY (US); Allan I. Krauter, Skaneateles, NY (US); Dale C. Saddlemire, Cortland, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 15/372,447

(22) Filed: Dec. 8, 2016

(65) Prior Publication Data

US 2017/0086661 A1   Mar. 30, 2017

Related U.S. Application Data

(63) Continuation of application No. 14/820,047, filed on Aug. 6, 2015, now Pat. No. 9,532,706.
(Continued)

(51) Int. Cl.
*A61B 1/32* (2006.01)
*A61B 1/06* (2006.01)
(Continued)

(52) U.S. Cl.
CPC ........ *A61B 1/0684* (2013.01); *A61B 1/00016* (2013.01); *A61B 1/00032* (2013.01);
(Continued)

(58) Field of Classification Search
CPC .......... A61B 1/0661; A61B 1/313; A61B 1/32
(Continued)

(56) References Cited

U.S. PATENT DOCUMENTS

| 34,110 A | 1/1862 | Gilbert |
|---|---|---|
| 245,515 A | 8/1881 | Lane |

(Continued)

FOREIGN PATENT DOCUMENTS

| CN | 2053088 U | 2/1990 |
|---|---|---|
| CN | 2156814 Y | 2/1994 |

(Continued)

OTHER PUBLICATIONS

International Search Report and Written Opinion for PCT/US2015/044152; dated Feb. 17, 2016; 16 pages.
(Continued)

*Primary Examiner* — Eduardo C Robert
*Assistant Examiner* — Christina Negrellirodriguez
(74) *Attorney, Agent, or Firm* — Barclay Damon LLP

(57) ABSTRACT

A speculum includes a first blade member and a second blade member, each of the first and second blade members having a distal end and an opposing proximal end. A portable illuminator having a light source and at least one battery includes a switch that is accessible through a slit or similar feature in the speculum. According to at least one version, the switch includes an extending tab portion that can extend through the slit or the end of a handle portion of the speculum to enable illumination. In another version, the portable illuminator can be attached to an articulation mechanism that is configured for moving the first and second blade members in relation to one another.

10 Claims, 16 Drawing Sheets

Related U.S. Application Data

(60) Provisional application No. 62/034,288, filed on Aug. 7, 2014.

(51) Int. Cl.
*A61B 1/303* (2006.01)
*A61B 1/00* (2006.01)
*A61B 1/07* (2006.01)

(52) U.S. Cl.
CPC ...... *A61B 1/00034* (2013.01); *A61B 1/00103* (2013.01); *A61B 1/00105* (2013.01); *A61B 1/06* (2013.01); *A61B 1/0669* (2013.01); *A61B 1/0676* (2013.01); *A61B 1/07* (2013.01); *A61B 1/303* (2013.01); *A61B 1/32* (2013.01)

(58) Field of Classification Search
USPC .................................. 600/184–246
See application file for complete search history.

(56) References Cited

U.S. PATENT DOCUMENTS

| | | |
|---|---|---|
| 299,532 A | 6/1884 | Fitch |
| 553,728 A | 1/1890 | Campbell |
| 3,162,376 A | 12/1964 | Furuya |
| 3,324,850 A | 6/1967 | Gunning et al. |
| 3,332,414 A | 7/1967 | Gasper |
| 3,373,737 A | 3/1968 | Moore et al. |
| 3,592,199 A | 7/1971 | Ostensen |
| 3,675,641 A | 7/1972 | Fiore |
| 3,716,047 A | 2/1973 | Moore et al. |
| 3,789,835 A | 2/1974 | Whitman |
| 3,841,318 A | 10/1974 | Olson |
| 3,851,642 A | 12/1974 | McDonald |
| 3,885,211 A | 5/1975 | Gutai |
| 3,934,578 A | 1/1976 | Heine |
| 3,945,371 A | 3/1976 | Adelman |
| 3,978,850 A | 9/1976 | Moore et al. |
| 3,985,125 A | 10/1976 | Rose |
| 4,067,323 A | 1/1978 | Troutner et al. |
| 4,156,424 A | 5/1979 | Burgin |
| 4,210,133 A | 7/1980 | Castaneda |
| 4,220,985 A | 9/1980 | Hukuba |
| 4,227,537 A | 10/1980 | Suciu et al. |
| 4,263,899 A | 4/1981 | Burgin |
| 4,300,541 A | 11/1981 | Burgin |
| 4,337,763 A | 7/1982 | Petrassevich |
| 4,432,351 A | 2/1984 | Hoary |
| 4,492,220 A | 1/1985 | Hayes |
| 4,502,468 A | 3/1985 | Burgin ............ A61B 1/24 600/184 |
| 4,517,628 A | 5/1985 | McDermott |
| 4,517,702 A | 5/1985 | Jackson |
| 4,546,761 A | 10/1985 | McCullough |
| 4,562,632 A | 1/1986 | Wilder et al. |
| 4,566,439 A | 1/1986 | Burgin |
| 4,597,383 A | 7/1986 | VanDerBel |
| 4,607,623 A | 8/1986 | Bauman |
| 4,619,248 A * | 10/1986 | Walsh ............ A61B 1/32 362/109 |
| 4,638,792 A | 1/1987 | Burgin |
| 4,646,722 A | 3/1987 | Silverstein et al. |
| 4,741,326 A | 5/1988 | Sidalle et al. |
| 4,763,678 A | 8/1988 | Ott |
| 4,766,887 A | 8/1988 | Cecil, Jr. et al. |
| 4,790,751 A | 12/1988 | Reinhardt et al. |
| 4,807,600 A | 2/1989 | Hayes |
| 4,811,937 A | 3/1989 | Rothman |
| 4,825,850 A | 5/1989 | Opie et al. |
| 4,869,238 A | 9/1989 | Opie et al. |
| 4,872,837 A | 10/1989 | Issalene et al. |
| 4,884,559 A | 12/1989 | Collins |
| 4,905,670 A | 3/1990 | Adair |
| 4,971,036 A | 11/1990 | Collins |
| 4,979,498 A | 12/1990 | Oneda et al. |
| 4,981,086 A | 1/1991 | Barca |
| 5,018,507 A | 5/1991 | Montaldi |
| 5,026,368 A | 6/1991 | Adair |
| 5,054,906 A | 10/1991 | Lyons, Jr. |
| 5,063,908 A | 11/1991 | Collins |
| 5,067,491 A | 11/1991 | Taylor, II et al. |
| 5,143,054 A | 9/1992 | Adair |
| 5,165,387 A | 11/1992 | Woodson |
| 5,174,278 A | 12/1992 | Babkow |
| 5,179,937 A | 1/1993 | Lee |
| 5,179,938 A | 1/1993 | Lonky |
| 5,201,908 A | 4/1993 | Jones |
| 5,222,271 A | 8/1993 | Eganhouse |
| 5,250,065 A | 10/1993 | Clement et al. |
| 5,284,474 A | 2/1994 | Adair |
| 5,306,237 A | 4/1994 | Clement et al. |
| 5,329,938 A | 7/1994 | Lonky |
| 5,337,734 A | 8/1994 | Saab |
| 5,338,292 A | 8/1994 | Clement et al. |
| 5,349,941 A | 9/1994 | Hori |
| 5,374,244 A | 12/1994 | Clement et al. |
| 5,388,817 A | 2/1995 | Jones |
| 5,394,863 A | 3/1995 | Sanford et al. |
| 5,458,122 A | 10/1995 | Yabe et al. |
| 5,465,709 A | 11/1995 | Dickie et al. |
| 5,491,834 A | 2/1996 | Chia |
| 5,595,344 A | 1/1997 | Stames |
| 5,639,238 A | 6/1997 | Fishburne, Jr. |
| 5,656,014 A | 8/1997 | Roone et al. |
| 5,695,492 A | 12/1997 | Brown |
| 5,711,921 A | 1/1998 | Langford |
| 5,716,329 A | 2/1998 | Dieter |
| 5,746,694 A | 5/1998 | Wilk |
| 5,772,435 A | 6/1998 | Dorman |
| 5,783,818 A | 7/1998 | Manabe et al. |
| 5,785,648 A | 7/1998 | Min |
| 5,836,764 A | 11/1998 | Buchanan |
| 5,840,013 A | 11/1998 | Lee et al. |
| 5,846,249 A | 12/1998 | Thompson |
| 5,865,729 A | 2/1999 | Meehan et al. |
| 5,873,820 A | 2/1999 | Norell |
| 5,899,854 A | 5/1999 | Slishman |
| 5,906,802 A | 5/1999 | Langford |
| 5,916,150 A | 6/1999 | Sillman |
| 5,916,151 A | 6/1999 | Charters |
| 5,921,777 A | 7/1999 | Dorman |
| 5,934,904 A | 8/1999 | Elrod et al. |
| 5,941,834 A | 8/1999 | Skladnev et al. |
| 5,961,937 A | 10/1999 | Gobbato |
| 6,004,265 A | 12/1999 | Hsu et al. |
| 6,030,210 A | 2/2000 | Bianchetti |
| 6,036,638 A | 3/2000 | Nwawka |
| 6,048,308 A | 4/2000 | Strong |
| 6,095,810 A | 8/2000 | Bianchetti |
| 6,102,851 A | 8/2000 | Mellin |
| 6,106,457 A | 8/2000 | Perkins et al. |
| 6,117,285 A | 9/2000 | Welch et al. |
| 6,130,520 A | 10/2000 | Wawro et al. |
| 6,159,162 A | 12/2000 | Kostylev et al. |
| 6,176,824 B1 | 1/2001 | Davis |
| 6,179,614 B1 | 1/2001 | Elrod et al. |
| 6,186,944 B1 | 2/2001 | Tsai |
| 6,217,512 B1 | 4/2001 | Salo et al. |
| 6,254,247 B1 | 7/2001 | Carson |
| 6,277,067 B1 | 8/2001 | Blair |
| 6,319,199 B1 | 11/2001 | Sheehan et al. |
| 6,346,085 B1 | 2/2002 | Schiffman |
| 6,361,489 B1 | 3/2002 | Tsai |
| 6,379,296 B1 | 4/2002 | Baggett |
| 6,379,299 B1 | 4/2002 | Borodulin et al. |
| 6,394,111 B1 | 5/2002 | Jacobs et al. |
| 6,394,950 B1 | 5/2002 | Weiss |
| 6,397,847 B1 | 6/2002 | Scarberry et al. |
| 6,432,045 B2 | 8/2002 | Lemperle et al. |
| 6,432,049 B1 * | 8/2002 | Banta ............ A61B 1/32 600/223 |
| 6,436,033 B2 | 8/2002 | Tan |
| 6,450,952 B1 | 9/2002 | Rioux et al. |

(56) References Cited

U.S. PATENT DOCUMENTS

| | | |
|---|---|---|
| 6,454,978 B1 | 9/2002 | Jacobs et al. |
| 6,468,232 B1 | 10/2002 | Ashton-Miller et al. |
| 6,487,440 B2 | 11/2002 | Deckert et al. |
| 6,494,964 B1 | 12/2002 | Jacobs et al. |
| 6,514,198 B2 | 2/2003 | Ishibiki |
| 6,516,817 B2 | 2/2003 | Jacobs |
| 6,516,818 B2 | 2/2003 | Jacobs |
| 6,524,259 B2 | 2/2003 | Baxter-Jones et al. |
| 6,569,091 B2 | 5/2003 | Diokno et al. |
| 6,585,727 B1 | 7/2003 | Cashman et al. |
| 6,589,168 B2 | 7/2003 | Thompson |
| 6,595,917 B2 | 7/2003 | Nieto |
| 6,610,020 B2 | 8/2003 | Voegele |
| 6,626,825 B2 | 9/2003 | Tsai |
| 6,663,576 B2 | 12/2003 | Gombrich et al. |
| 6,739,744 B2 | 5/2004 | Williams et al. |
| 6,743,198 B2 | 6/2004 | Tihon |
| 6,761,687 B1 | 7/2004 | Doshi et al. |
| 6,830,547 B2 | 12/2004 | Weiss |
| 6,889,832 B2 | 5/2005 | Gabele |
| 6,895,965 B2 | 5/2005 | Scarberry et al. |
| 6,896,653 B1 | 5/2005 | Vail, III |
| 6,908,428 B2 | 6/2005 | Aizenfeld et al. |
| 6,929,601 B2 | 8/2005 | Nakao |
| 6,957,897 B1 | 10/2005 | Nelson et al. |
| 6,974,294 B2 | 12/2005 | Pressman |
| 7,014,340 B2 | 3/2006 | Bettis |
| 7,018,592 B2 | 3/2006 | Bowen |
| 7,021,798 B2 | 4/2006 | Tsimerman |
| 7,029,439 B2 | 4/2006 | Roberts et al. |
| 7,060,039 B2 | 6/2006 | Voegele |
| D562,762 S | 2/2008 | Saddlemire et al. |
| D584,689 S | 1/2009 | Slawson et al. |
| 7,499,760 B2 | 3/2009 | Rose et al. |
| 7,631,981 B2 | 12/2009 | Miller ............... A61B 1/00103 362/119 |
| 7,758,203 B2 | 7/2010 | McMahon et al. |
| 8,096,945 B2 | 1/2012 | Buchok et al. |
| 8,142,352 B2 | 3/2012 | Vivenzio ............... A61B 1/303 600/186 |
| 8,157,728 B2 | 4/2012 | Danna et al. |
| 8,376,942 B2 | 2/2013 | Krauter et al. |
| 8,435,175 B2 | 5/2013 | McMahon et al. |
| 8,821,395 B2 | 9/2014 | McMahon et al. |
| 2001/0029044 A1 | 10/2001 | Gombrich et al. |
| 2001/0029387 A1 | 10/2001 | Wolf et al. |
| 2001/0033805 A1 | 10/2001 | Jacobs et al. |
| 2001/0034917 A1 | 11/2001 | DuCey |
| 2002/0016525 A1 | 2/2002 | Ishibiki |
| 2002/0022769 A1 | 2/2002 | Smith et al. |
| 2002/0038075 A1 | 3/2002 | Tsai |
| 2002/0038076 A1 | 3/2002 | Sheehan et al. |
| 2002/0055670 A1 | 5/2002 | Weiss |
| 2002/0058230 A1 | 5/2002 | Savin et al. |
| 2002/0083547 A1 | 7/2002 | Kessler |
| 2002/0114803 A1 | 8/2002 | Deaver et al. |
| 2002/0119419 A1 | 8/2002 | Suzuki et al. |
| 2002/0120210 A1 | 8/2002 | Voegele |
| 2002/0125666 A1 | 9/2002 | Bidwell |
| 2002/0134255 A1 | 9/2002 | Svenka et al. |
| 2002/0137006 A1 | 9/2002 | Gugel et al. |
| 2002/0137008 A1 | 9/2002 | McSpadden et al. |
| 2002/0156350 A1 | 10/2002 | Nieto |
| 2002/0156395 A1 | 10/2002 | Stephens et al. |
| 2002/0162304 A1 | 11/2002 | Stravitz |
| 2002/0165433 A1 | 11/2002 | Stihl |
| 2002/0165435 A1 | 11/2002 | Weiss |
| 2002/0170133 A1 | 11/2002 | McDevitt et al. |
| 2002/0198471 A1 | 12/2002 | Baxter-Jones et al. |
| 2003/0139673 A1 | 7/2003 | Vivenzio et al. |
| 2003/0158502 A1 | 8/2003 | Baxter-Jones et al. |
| 2003/0164182 A1 | 9/2003 | Jacobs et al. |
| 2003/0176772 A1 | 9/2003 | Yang |
| 2003/0187331 A1 | 10/2003 | Faludi et al. |
| 2003/0188761 A1 | 10/2003 | Garcia et al. |
| 2003/0195434 A1 | 10/2003 | Voegele |
| 2003/0208995 A1 | 11/2003 | Sravitz |
| 2003/0213074 A1 | 11/2003 | Kawazoe et al. |
| 2003/0213082 A1 | 11/2003 | Tanaka |
| 2004/0014000 A1 | 1/2004 | Bernhard |
| 2004/0026829 A1 | 2/2004 | Van Der Weegen |
| 2004/0059253 A1 | 3/2004 | Martone et al. |
| 2004/0076019 A1 | 4/2004 | Tsimerman et al. |
| 2004/0083681 A1 | 5/2004 | Stravitz |
| 2004/0084056 A1 | 5/2004 | Tyndal |
| 2004/0084070 A1 | 5/2004 | Sasaki et al. |
| 2004/0118440 A1 | 6/2004 | Sasaki et al. |
| 2004/0141175 A1 | 7/2004 | Baldwin et al. |
| 2004/0166474 A1 | 8/2004 | Gugel et al. |
| 2004/0183482 A1 | 9/2004 | Roberts et al. |
| 2004/0184288 A1 | 9/2004 | Bettis |
| 2004/0186355 A1 | 9/2004 | Strong et al. |
| 2004/0190140 A1 | 9/2004 | Bala |
| 2004/0191723 A1 | 9/2004 | Shearer et al. |
| 2004/0225267 A1 | 11/2004 | Tapadiya |
| 2005/0021017 A1 | 1/2005 | Karasawa et al. |
| 2005/0033119 A1 | 2/2005 | Okawa et al. |
| 2005/0054894 A1 | 3/2005 | Aizenfeld et al. |
| 2005/0065496 A1 | 3/2005 | Simon |
| 2005/0065699 A1 | 4/2005 | Weiss |
| 2005/0071939 A1 | 4/2005 | McDevitt et al. |
| 2005/0080462 A1 | 4/2005 | Jenkins et al. |
| 2005/0125027 A1 | 6/2005 | Knodel et al. |
| 2005/0137613 A1 | 6/2005 | Kasahara et al. |
| 2005/0148819 A1 | 7/2005 | Noguchi et al. |
| 2005/0159649 A1 | 7/2005 | Patel |
| 2005/0159752 A1 | 7/2005 | Walker et al. |
| 2005/0162028 A1 | 7/2005 | Kardeis et al. |
| 2005/0192482 A1 | 9/2005 | Carpenter et al. |
| 2005/0209507 A1 | 9/2005 | Suzuki et al. |
| 2005/0214681 A1 | 9/2005 | Azamia et al. |
| 2005/0215858 A1 | 9/2005 | Vail, III |
| 2005/0222601 A1 | 10/2005 | Erhard |
| 2005/0236230 A1 | 10/2005 | Fee |
| 2005/0261763 A1 | 11/2005 | Wang |
| 2005/0274093 A1 | 12/2005 | Stravitz et al. |
| 2005/0277811 A1 | 12/2005 | Richards et al. |
| 2006/0004271 A1 | 1/2006 | Peyser et al. |
| 2006/0027246 A1 | 2/2006 | Wilkinson |
| 2006/0029901 A1 | 2/2006 | Rose et al. |
| 2006/0037165 A1 | 2/2006 | McDevitt et al. |
| 2006/0041274 A1 | 2/2006 | Su |
| 2006/0046226 A1 | 2/2006 | Bergler et al. |
| 2006/0069529 A1 | 4/2006 | Tartaglia et al. |
| 2006/0084843 A1 | 4/2006 | Sommerich et al. |
| 2006/0085923 A1 | 4/2006 | Santos |
| 2006/0104856 A1 | 5/2006 | Farrell |
| 2006/0110700 A1 | 5/2006 | Cipolla et al. |
| 2006/0116551 A1 | 6/2006 | Lovett et al. |
| 2006/0127844 A1 | 6/2006 | Michaelian |
| 2006/0130438 A1 | 6/2006 | Stravitz et al. |
| 2006/0137122 A1 | 6/2006 | Ryan |
| 2007/0156022 A1 | 7/2007 | Patel |
| 2007/0179342 A1* | 8/2007 | Miller ............... A61B 1/267 600/188 |
| 2007/0230164 A1 | 10/2007 | Vivenzio et al. |
| 2007/0230167 A1 | 10/2007 | McMahon et al. |
| 2008/0004498 A1 | 1/2008 | Pecherer |
| 2008/0269565 A1 | 10/2008 | McMahon et al. |
| 2009/0198108 A1 | 8/2009 | Chen et al. |
| 2009/0216088 A1 | 8/2009 | Danna et al. |
| 2009/0287192 A1 | 11/2009 | Vivenzio et al. |
| 2012/0078060 A1* | 3/2012 | Swift ............... A61B 17/42 600/220 |
| 2012/0209079 A1 | 8/2012 | McMahon et al. |
| 2014/0039266 A1 | 2/2014 | Porat |
| 2014/0148653 A1 | 5/2014 | McMahon et al. |

FOREIGN PATENT DOCUMENTS

| | | |
|---|---|---|
| CN | 2387854 Y | 7/2000 |
| CN | 2516109 Y | 10/2002 |
| CN | 2516526 Y | 10/2002 |
| CN | 2549898 Y | 5/2003 |

(56) References Cited

FOREIGN PATENT DOCUMENTS

| | | | |
|---|---|---|---|
| CN | 2629738 Y | 8/2004 |
| CN | 1565664 A | 1/2005 |
| CN | 2668152 Y | 1/2005 |
| CN | 2879957 Y | 3/2007 |
| CN | 201996525 U | 10/2011 |
| CN | 203000892 U | 6/2013 |
| CN | 103860134 A | 6/2014 |
| EP | 0 190 014 B1 | 3/1994 |
| FR | 2490478 A1 | 3/1982 |
| GB | 553 728 | 6/1943 |
| WO | WO 98/25512 | 6/1998 |
| WO | WO 03/082123 A2 | 10/2003 |
| WO | WO 2004/037287 A2 | 5/2004 |
| WO | WO 2006/107877 A2 | 10/2006 |
| WO | WO 2006/107878 A2 | 10/2006 |
| WO | WO 2006/121530 A2 | 11/2006 |
| WO | WO 2006/122031 A2 | 11/2006 |
| WO | WO 2008/080033 A2 | 7/2008 |
| WO | WO 2008/080040 A1 | 7/2008 |
| WO | WO 2009/149232 A2 | 12/2009 |
| WO | WO 2013/114108 A1 | 8/2013 |

OTHER PUBLICATIONS

Chinese Office Action and Search Report for CN 201210247067.6; dated Mar. 31, 2014; 8 pages.
European Office Action for EP Application No. 06 749 170.4; dated Jan. 17, 2011; 4 pages.
Supplementary European Search Report for EP Application No. 06 769 794.6; dated May 8, 2009; 9 pages.
Supplementary European Search Report for EP Application No. 06 749 169.6; dated May 8, 2009; 9 pages.
Supplementary European Search Report for EP Application No. 06 749 170.4; dated May 8, 2009; 13 pages.
International Search Report/Written Opinion (ISR/WO); dated Jun. 5, 2008 (7 pages).
Chinese Office Action for CN 201580054359.X; dated Nov. 27, 2017; 13 pages.
Chinese Office Action for CN 201580054359.X; dated May 30, 2018; 11 pages.
Chinese Notice of Refusal for CN 201580054359.X; dated Oct. 15, 2018; 16 pages.
Chinese Notification of Re-Examination for CN 201580054359.X; dated Aug. 28, 2019; 14 pages.
Chinese Decision of Re-Examination for CN 201580054359.X; dated Mar. 19, 2020; 19 pages.

* cited by examiner

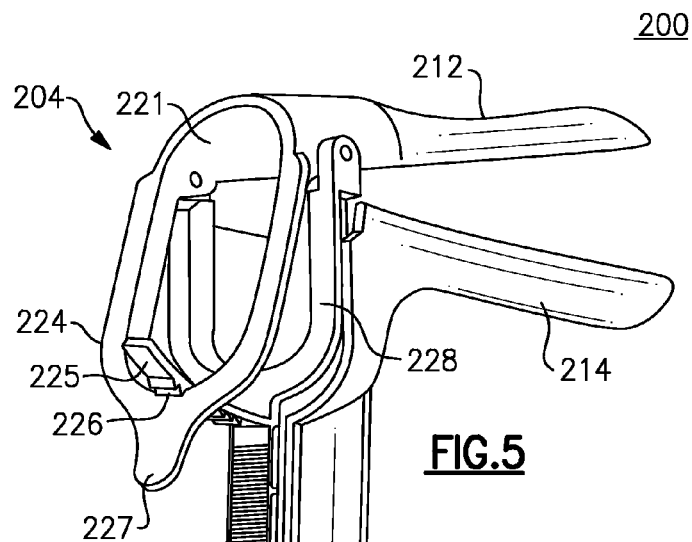
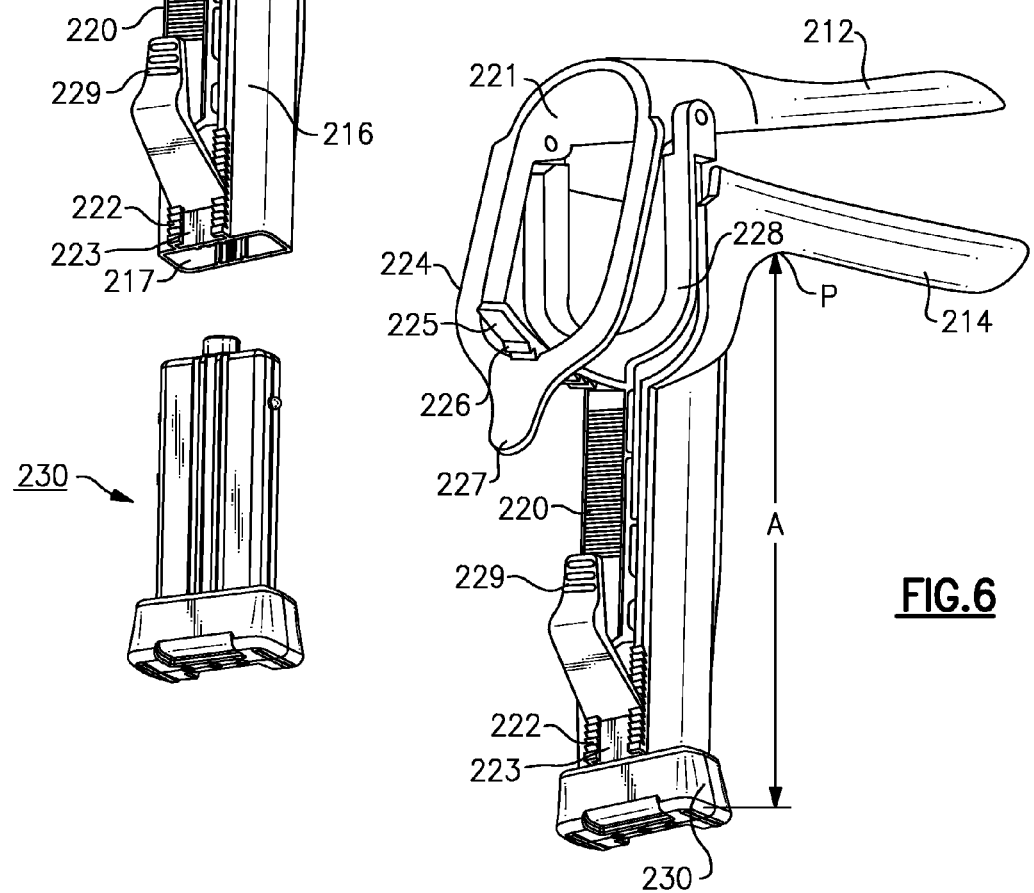

VAGINAL SPECULUM WITH ILLUMINATOR

CROSS REFERENCE TO RELATED APPLICATION

This patent application is a continuation of U.S. patent application Ser. No. 14/820,047, filed Aug. 6, 2015 and entitled "Vaginal Speculum with Illuminator", which is a non-provisional application of U.S. Provisional Patent Application Ser. No. 62/034,288, filed Aug. 7, 2014, and entitled "Vaginal Speculum with Illuminator, the entire contents of each application being incorporated herein by reference.

TECHNICAL FIELD

This application generally relates to the field of diagnostic medicine, and more specifically to a vaginal speculum assembly having a portable illuminator.

BACKGROUND

The conduction of vaginal diagnostic examinations using a speculum requires the proper application of directed light without interfering with the ability to view the intended target (e.g., the cervix) of the patient.

The specula presently used with illuminators commonly incorporate upper and lower blade members, as well as an articulation mechanism that is used for moving the upper and lower blade members in relation to one another in order to permit dilation of a patient. The rear of the speculum typically includes at least one aperture to enable viewing of the target.

Due to the increased ease and miniaturization of components, such as batteries and LEDs, there is a further need to improve the portability and accessibility of illuminators presently used in connection with medical diagnostic apparatus, including vaginal specula as well as a need to reduce the overall costs in terms of consumed material and manufacture of such apparatus. For example, a curved light pipe is presently used in specula in which an illuminator is disposed within a receiving cavity of a handle portion, the illuminator being coupled to the proximal end of the light pipe which has a light emitting end. The incorporation of the foregoing structure requires a considerable amount of material, which adds cost and complexity to the manufacture of the speculum. To that end, there is a need to more directly direct light to the medical target of interest. It is therefore a general need in the field to improve upon the accessibility and design of such apparatus.

BRIEF DESCRIPTION

Therefore and according to one aspect, there is described a vaginal speculum comprising a first blade member and a second blade member, each of the first and second blade members including opposing distal and proximal ends. The speculum further comprises an illuminator having a light source and at least one battery for powering the light source, the illuminator further including a switch. The switch is movable from a first position to a second position to selectively energize the light source, with the speculum having at least one slit enabling access to the movable switch. In one version, the switch includes an extending tab portion that energizes the light source when pulled from the illuminator.

The speculum can include a handle portion extending downwardly from the second blade member, the handle portion defining a cavity extending between a distal end and a proximal end thereof. In one version, the at least one slit can be provided on at least one of the first blade member, the second blade member or the handle portion. In another version, the illuminator can be attached to one of the upper and lower blade members, with the tab portion extending through the handle portion and extending from the end of the defined cavity.

In another version, a speculum comprises a first blade member and a second blade member, each of the first and second blade members having a distal end and an opposing proximal end. An articulation mechanism interconnecting the first and second blade members is configured for moving the first and second blade members in relation to one another. A portable illuminator is attached to the articulation mechanism.

In one exemplary version, the articulation mechanism comprises a lever member extending from the proximal end of the first blade member and a yoke that is attached to the proximal end of the second blade member. Each of the lever member and yoke are connected to one another to permit relative movement of the first and second blade members to effect dilation of a patient.

According to at least one embodiment, the portable illuminator can be releasably attached to the articulation mechanism or otherwise secured thereto. For example, the illuminator can be releasably attached or fixedly secured to one of the lever member and the yoke while preferably maintaining visibility of a target of interest by the user through a defined aperture of the speculum.

For example, the lever member and the yoke can each define a rear viewing aperture, enabling access to a spacing between the distal ends of the first and second blade members and in which the portable illuminator is configured to direct light distally through at least one of the viewing apertures towards the distal end of the blade members and towards a target of interest.

In at least one embodiment, the portable illuminator comprises a housing containing at least one battery and a light source. The light source can comprise at least one LED. An actuable switch selectively energizes and deenergizes the contained light source. The switch can be provided in relation to the housing. In at least one version, the switch can be externally disposed relative to the housing for direct access. According to at least one embodiment, the switch can comprise an extending tab that can be pulled from the housing in order to energize the contained light source.

The speculum can include a handle portion downwardly extending from the proximal end of the lower blade member. The handle portion can include a distal end and a proximal end and in which the extending tab portion extends into the interior of the handle portion and is accessible through the proximal end of the handle portion. In another version, the tab portion can extend through a lateral wall of the handle portion and more specifically through at least one defined slit.

According to yet another aspect, there is provided a speculum comprising an upper blade member and a lower blade member. Each of the upper and lower blade members includes a distal end and a proximal end. A portable illuminator comprising at least one battery and a light source is sized to fit at least partially within the distal end of one of the upper and lower blade members.

In at least one version, the housing of the portable illuminator can fit entirely within a trough-shaped blade portion of one of the upper and lower blade members.

According to yet another aspect, there is provided a speculum comprising a first blade member and a second blade member. Each of the first and second blade members include a distal end and an opposing proximal end. The speculum further comprises a portable illuminator having a light source and at least one battery wherein the portable illuminator is non-removably secured to the speculum.

According to still another aspect, there is provided a vaginal speculum comprising a first blade member and a second blade member, each of the first and second blade members including opposing distal and proximal ends. A handle portion downwardly extending from the proximal end of the second blade member has a distal end at the second blade member and an opposing proximal end, the handle portion further includes a cavity having an open end at the proximal end. The speculum further comprises an illuminator comprising a light source and at least one battery for powering the light source as well as a switch movable from a first position to a second position to selectively energize the light source, the switch comprising a movable tab portion that is accessible through the open end of the handle portion.

One advantage realized by the herein described concepts is that of improved illumination of the target using a vaginal speculum, which therefore provides better results in terms of performing pelvic examinations of patients. The herein described speculum assembly is easier to manufacture than prior known versions and in which less material is required.

Another advantage realized is that the entire speculum assembly, including the illuminator, can be made as a disposable or for single patient use.

Yet another advantage is that the above speculum assembly can be manufactured more inexpensively, but with no tradeoffs in terms of reliability.

These and other features and advantages will be readily apparent from the following Detailed Description, which should be read in conjunction with the accompanying drawings.

BRIEF DESCRIPTION OF THE DRAWINGS

FIG. 5 is a partially sectioned view of another known vaginal speculum assembly including a portable illuminator prior to assembly;

FIG. 6 depicts the vaginal speculum assembly of FIG. 5 in an assembled condition;

DETAILED DESCRIPTION

Figure 1:
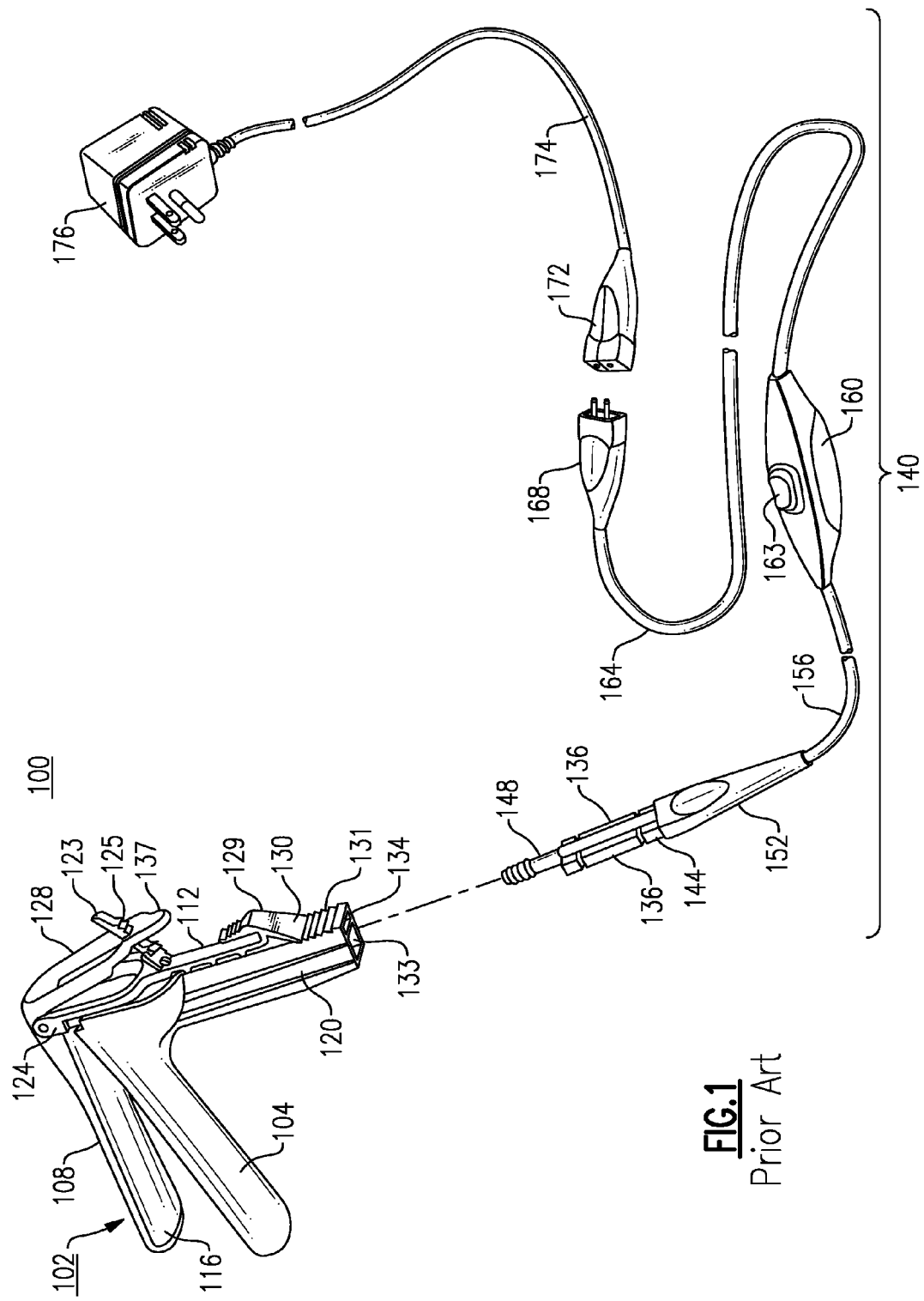
FIG. 1 is a perspective view of a known vaginal speculum assembly including a tethered illuminator.
Figure 2:
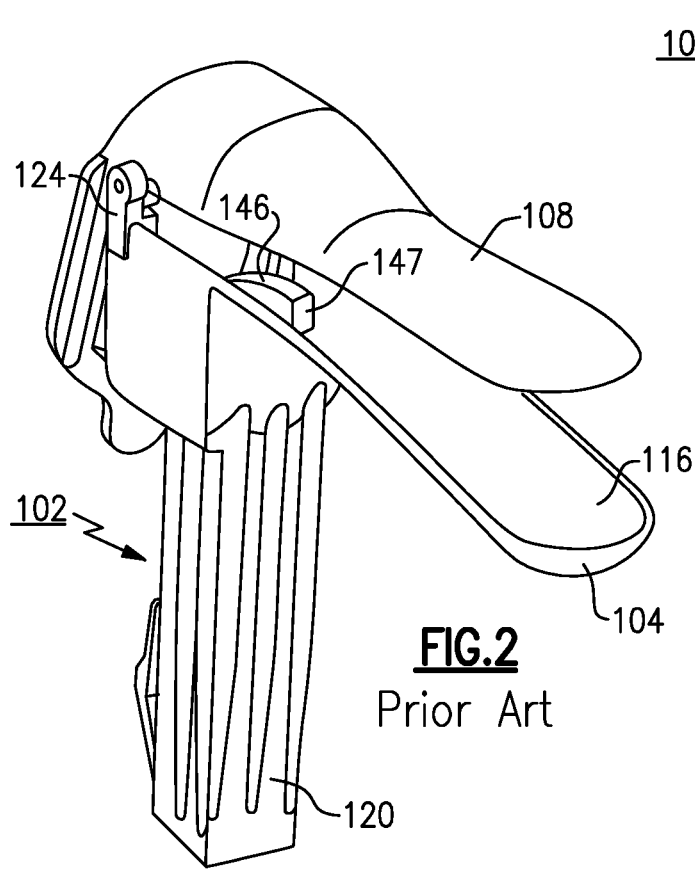
FIG. 2 is a top perspective view of the prior art disposable speculum shown in FIG. 1.

The following description relates to a vaginal speculum assembly that includes an illuminator, as described in accordance with a number of exemplary embodiments. Throughout the course of discussion, certain terms are used in an effort to adequately provide a suitable frame of reference in regard to the accompanying drawings. These terms, which may include "external", "internal", "distal", "proximal", "inner", "outer", "above", "below", "front", "rear", "interior", "exterior" and the like are not intended to limit the scope of the inventive concepts described and claimed herein, unless so specifically indicated.

For purposes of background, a known vaginal speculum apparatus 100 developed by Applicant includes a disposable speculum 102 and a reusable and tethered illumination assembly 140, as shown in FIGS. 1-4. The disposable speculum 102 includes three (3) interconnected components; namely, a lower or bottom blade member 104, an upper or top blade member 108 and a slide member 112. Each of the two blade members 104, 108 is preferably made from a clear, durable plastic material, such as acrylic or polystyrene, wherein the lower blade member 104 and upper blade member 108 commonly include a trough-shaped distal blade portion 116. A handle portion 120 extends vertically downward from the proximal or rear end of the lower blade member 104, wherein the handle portion 120 is integrally molded as part of the lower blade member 104.

An intermediate portion of the slide member 112 is fitted within a guide slot (not shown) that is provided on a rearward facing side of the handle portion 120, the slide member further having a forked upper end or yoke 124 that receives the upper blade member 108, which is pivotally attached thereto, including a downwardly extending lever portion 128 extending from the proximal end of the upper blade member 108.

Figure 3:
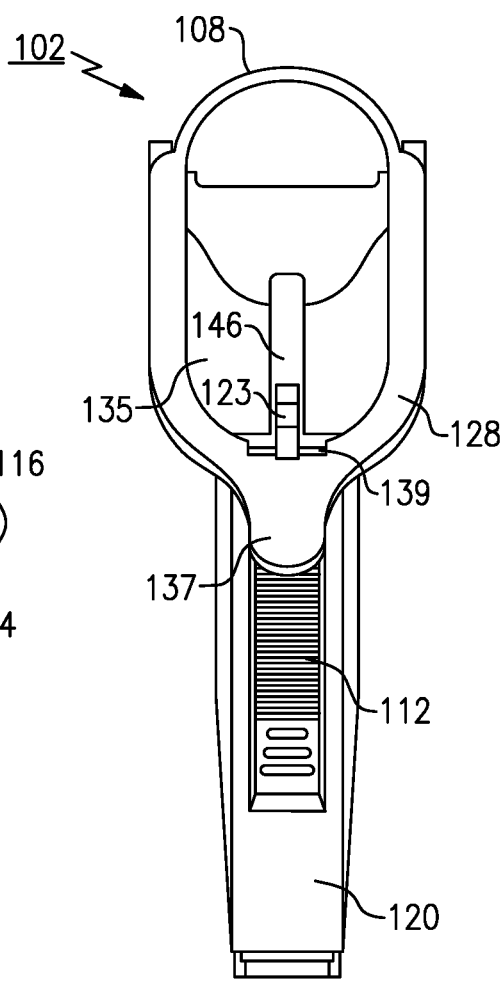
FIG. 3 is a rear facing view of the disposable speculum of FIGS. 1 and 2.
Figure 4:
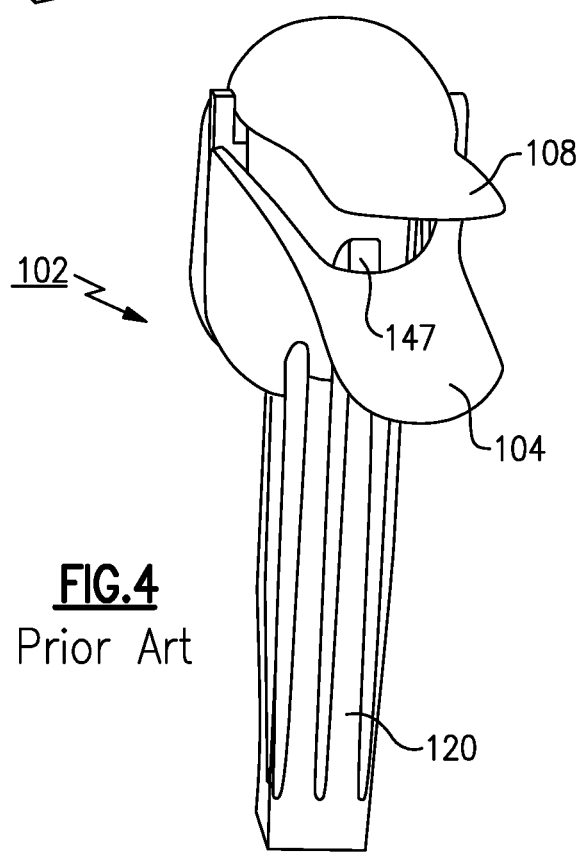
FIG. 4 is a front perspective view of the disposable speculum of FIGS. 1-3.

The lever portion 128 further includes an opening 135, shown only in FIG. 3, defining a user aperture while the yoke 124 defines another aligned user aperture between the upper and lower blade members 104, 108. The lever portion 128 terminates in a tab 137, the latter having an interior slot 139. The interior slot 139 is engageable with a flexible rear extending arcuate projection 123 of the yoke/slide member, and more particularly with a set of ratchet teeth 125 that are provided on a downward facing surface of the projection 123. The ratchet teeth 125 of the flexible projection 123 are biased into the interior slot 139 of the lever portion 128 of the upper blade member 108. Angular articulation between the upper and lower blade members 104, 108 is initiated by applying finger pressure inwardly against the tab 137, causing the lever portion 128 to move along the set of ratchet teeth 125, and providing positive engagement therewith.

In addition, the slide member 112 further includes a lower tongue 129 having a single ratchet tooth 130 that engages with a set of corresponding teeth 131 provided on the rear exterior side of the handle portion 120 in order to provide relative vertical adjustment between the upper and lower blade members 104, 108, as needed. Additional details relating to the disposable speculum 102, including the adjustability of the upper and lower blade members 104, 108 is provided in U.S. Pat. No. 3,716,047, the relevant portions being incorporated by reference herein.

Still referring to FIGS. 1-4, the handle portion 120 of the disposable speculum 102 includes a receiving cavity 133 that is sized and configured for receiving a housing 144 of the reusable illumination assembly 140. The housing 144 retains a miniature incandescent lamp, such as a halogen bulb (not shown), which is sealingly retained within a distal portion 148 of the housing 144. A proximal portion of the housing 144 extending from the receiving cavity 133, as shown in FIG. 1 and when assembled to the speculum 102, includes a strain relief 152 extending to an electrical cable 156 that further extends to a switch assembly 160. As shown in FIG. 1, an electrical cable 164 extends from the switch assembly 160 to a pronged plug 168 that is configured to engage a corresponding female plug 172, the latter being tethered by a corresponding cable 174 to a power supply transformer 176. The switch assembly 160 is defined by an elastomeric housing having a depressible button 163 that is used to selectively energize the miniature incandescent lamp (not shown) retained within the distal portion 148 of the illuminator housing 144. Additional details relating to the illumination assembly 140 are found in U.S. Patent Application Publication No. 2004/0184288A1, the entire contents of which are herein incorporated by reference.

In addition, the disposable speculum 102 includes a curved light pipe or tube 146 that is used to direct the output of the illumination assembly 140 to the target of interest. The light pipe 146 includes a proximal end disposed in the upper end of the handle portion 120 of the lower blade member 104. When the illumination housing 144 is inserted into the receiving cavity 133 of the handle portion 120, the contained incandescent lamp is optically coupled to the proximal end of the light pipe 146. Emitted light is then directed by means of internal reflection through the length of the light pipe 146 to a distal light emitting end 147. The light is distributed substantially along a longitudinal axis of the lower blade member 104 toward the distal end of the trough-shaped portion 116 and toward the target through an opening defined between the blade members 104, 108. The light pipe 146 is preferably molded directly into the lower blade member 104, wherein the proximal end of the light pipe 146 is provided in the upper end of the receiving cavity 133 of the handle portion 120.

In operation, light from the coupled incandescent lamp is collected by the proximal end of the light pipe 146 and conducted therethrough. The target of interest can be adequately viewed through the rear viewing apertures of the speculum 102 without substantial interference.

More recently, Applicant has developed another vaginal speculum assembly 200, herein shown in FIGS. 5-9. Like the preceding version, the vaginal speculum assembly 200 includes a disposable speculum 204 and an illumination assembly 230 that is releasably attached to the handle portion 216 of the speculum 204. Also and as in the preceding version, a handle portion 216 of the speculum 204 is essentially hollow, including an open bottom end extending into an otherwise enclosed receiving cavity 217.

The disposable speculum 204 according to this assembly 200 is defined by an upper or top blade member 212, a lower or bottom blade member 214 (which integrally includes the handle portion 216) and a slide member 220. Each of the upper and lower blade members 212, 214 is similarly constructed to the version described in FIGS. 1-4 and preferably formed from a durable clear plastic material, such as an acrylic or polystyrene. In addition, each blade member 212, 214 further is defined by a trough-shaped elongate distal section or blade 215. The upper blade member 212 further includes a lever portion 224 extending downwardly at its proximal end thereof. The slide member 220, also preferably made from a durable plastic material, though not necessarily clear, further includes an upper forked portion or yoke 228 that pivotally receives the upper blade member 212, as well a flexible arcuate projection 225 that is disposed immediately below the yoke 228 and extends rearward; that is, in a proximal direction away from the handle portion 216. The flexible projection 225 is upwardly curved in an arcuate configuration, FIG. 5, and includes a set of ratchet teeth 226 that are disposed along a downward facing surface thereof.

The lever portion 224 is defined by a frame-like structure that includes an opening 221, defining an aperture along with the forked portion of the yoke 228 through which the user can examine the patient through the upper and lower blade members 212, 214, the lever portion having a bottom tab 227 that can engage the flexible projection 225 and more specifically the ratchet teeth 226. Finger pressure applied onto the bottom tab 227 allows the user to angularly articulate or move the blade members 212, 214 of the speculum 204. In addition, an intermediate portion of the slide member 220 is movably (axially) disposed within a guide slot 223 extending over the entirety of the length of the rear side of the handle portion 216. Finger pressure on the lower tongue 229 of the slide member 220 permits engagement between a single tooth provided on the lower tongue 229 and a set of external teeth 222 provided on the proximal (rear) side of the handle portion 216 to enable selective vertical articulation (spacing) of the lower blade member 214 with respect to the upper blade member 212. The guide slot 223 extends axially through the set of external teeth 222. The foregoing speculum 202 is described in greater detail in U.S. Pat. No. 8,435,175 B2, the entire contents of which are incorporated by reference herein.

According to this version, the speculum 204 is adapted to interchangeably receive the tethered illumination assembly 140, FIG. 1, within the receiving cavity 217, as well as the portable illumination assembly 230.

Figure 7:
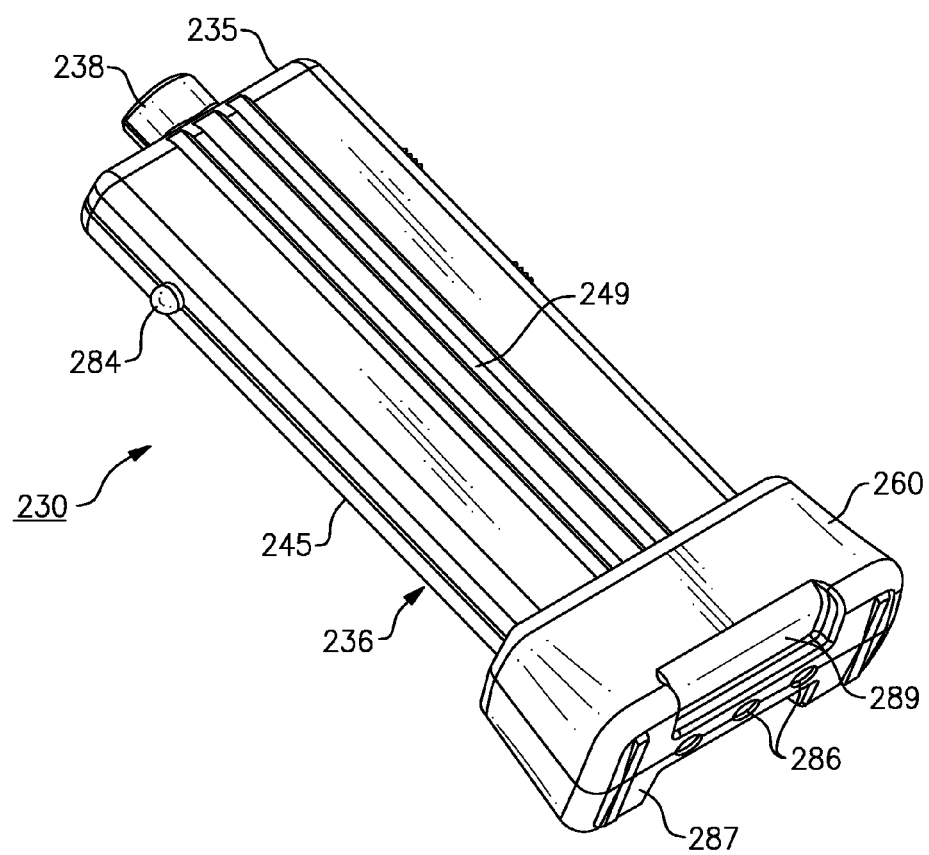
FIG. 7 is a perspective view of the portable illuminator of FIGS. 5 and 6.
Figure 8:
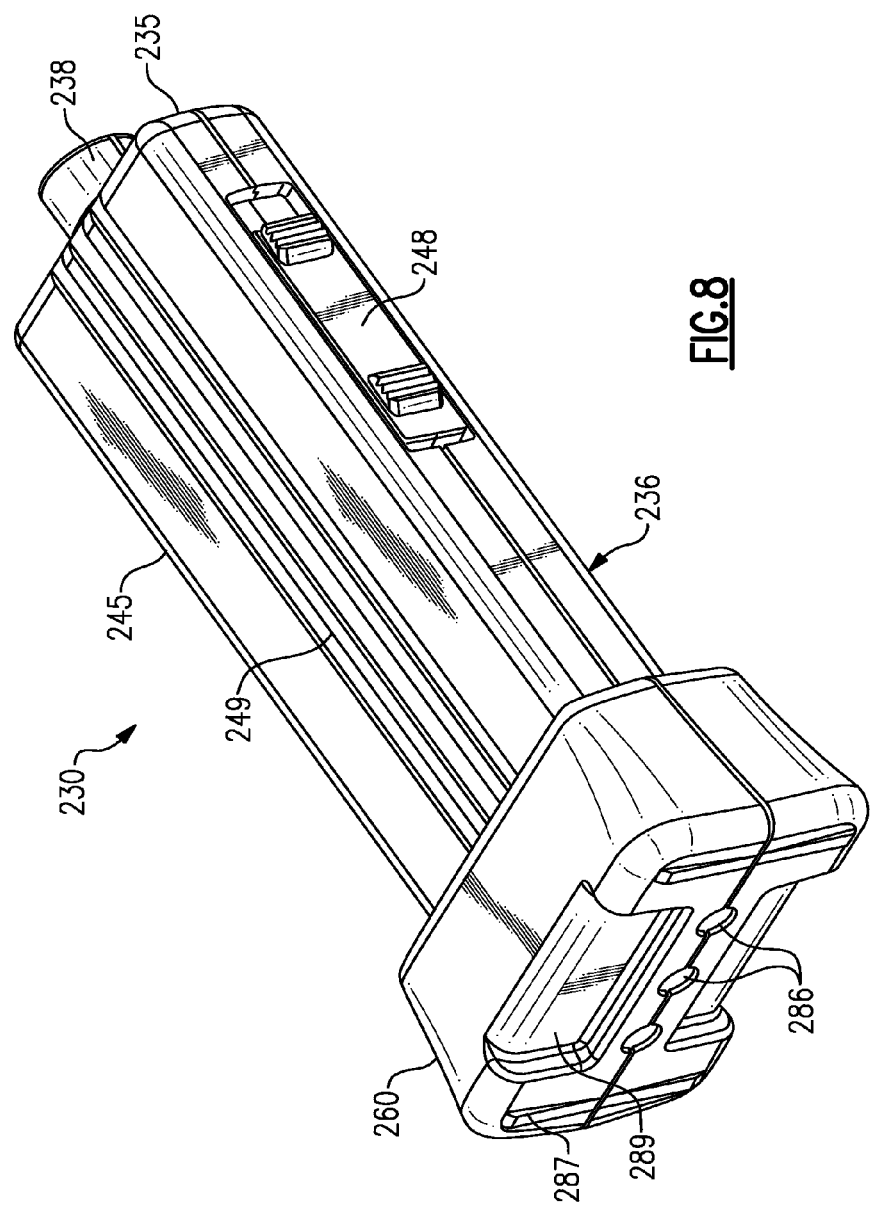
FIG. 8 is another perspective view of the portable illuminator of FIGS. 5-7.
Figure 9:
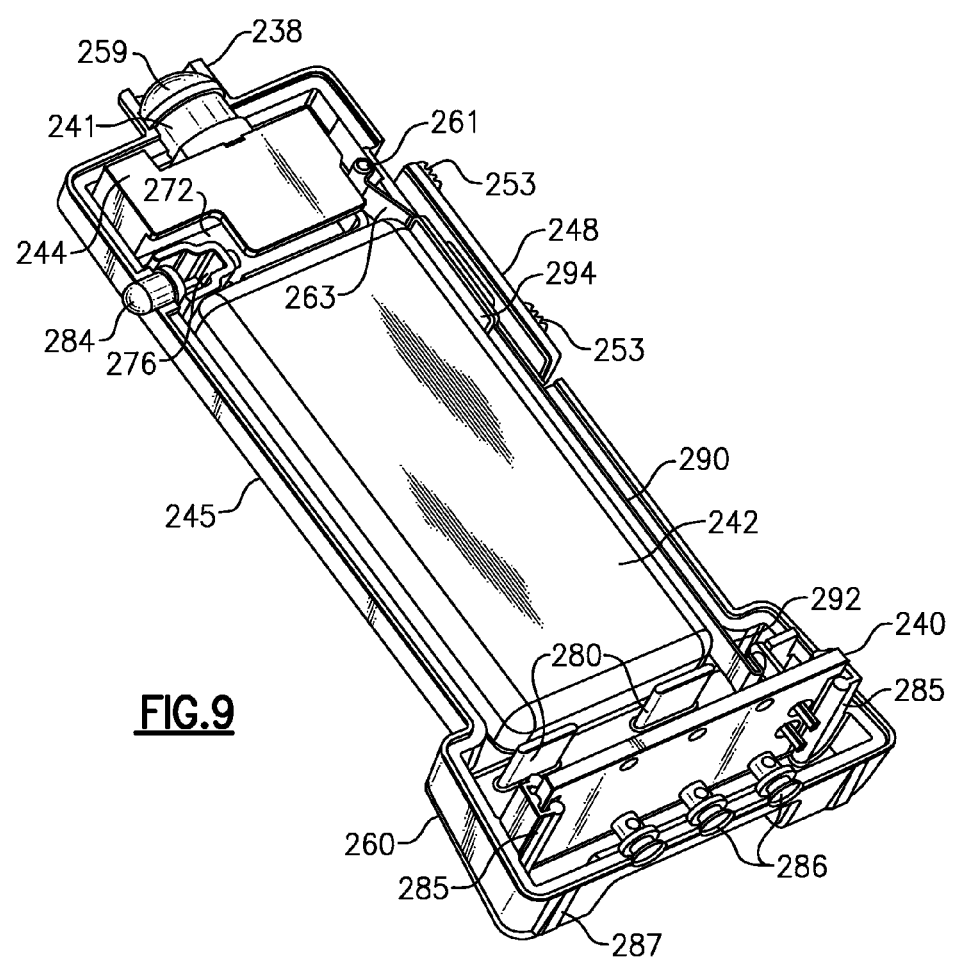
FIG. 9 is a sectioned perspective view of the portable illuminator of FIGS. 5-8.
Figure 10:
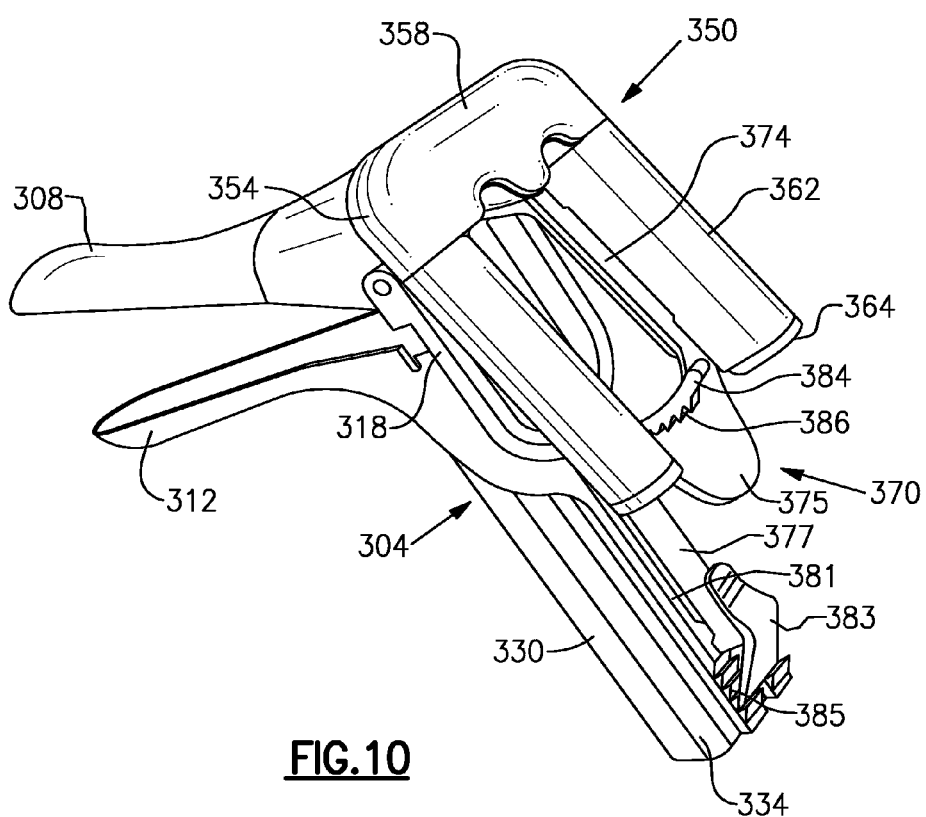
FIG. 10 is a rear perspective view of a vaginal speculum assembly made in accordance with an exemplary embodiment.
Figure 11:
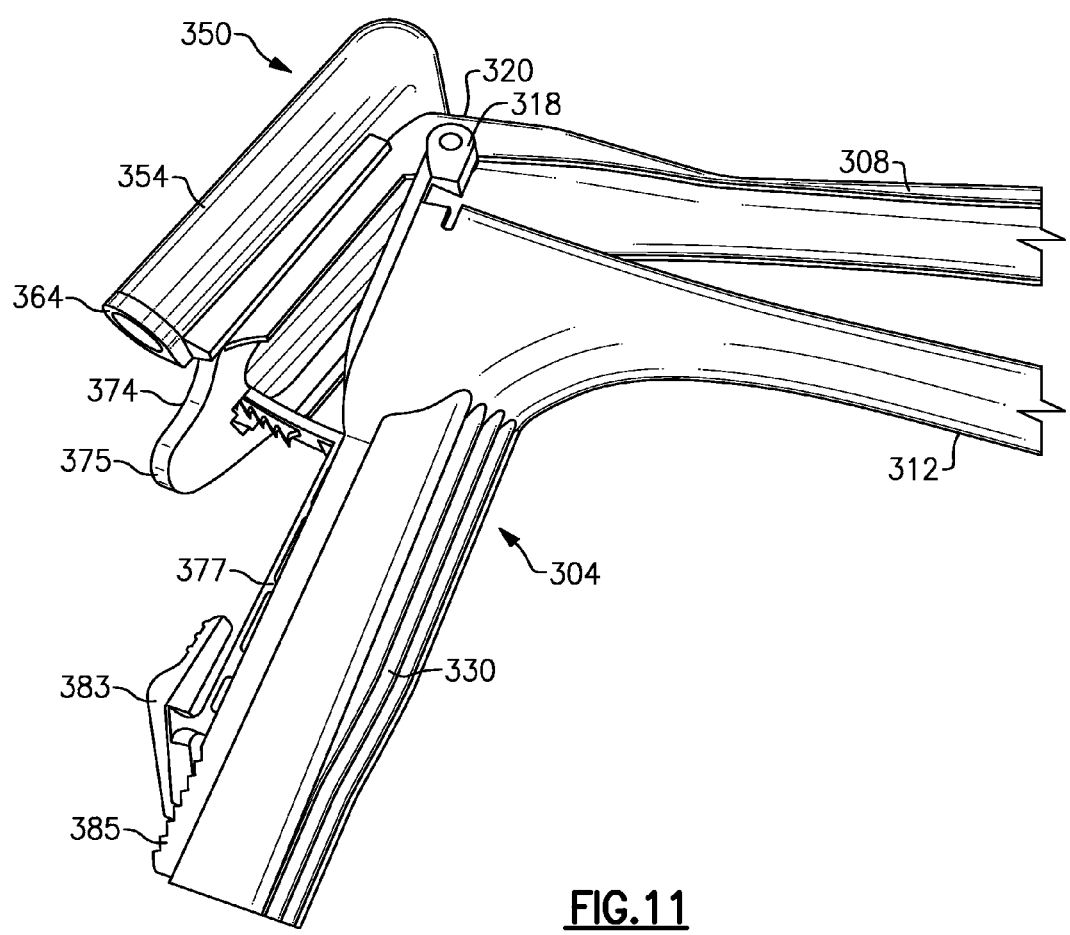
FIG. 11 is a side perspective view of the vaginal speculum assembly of FIG. 10.
Figure 12:
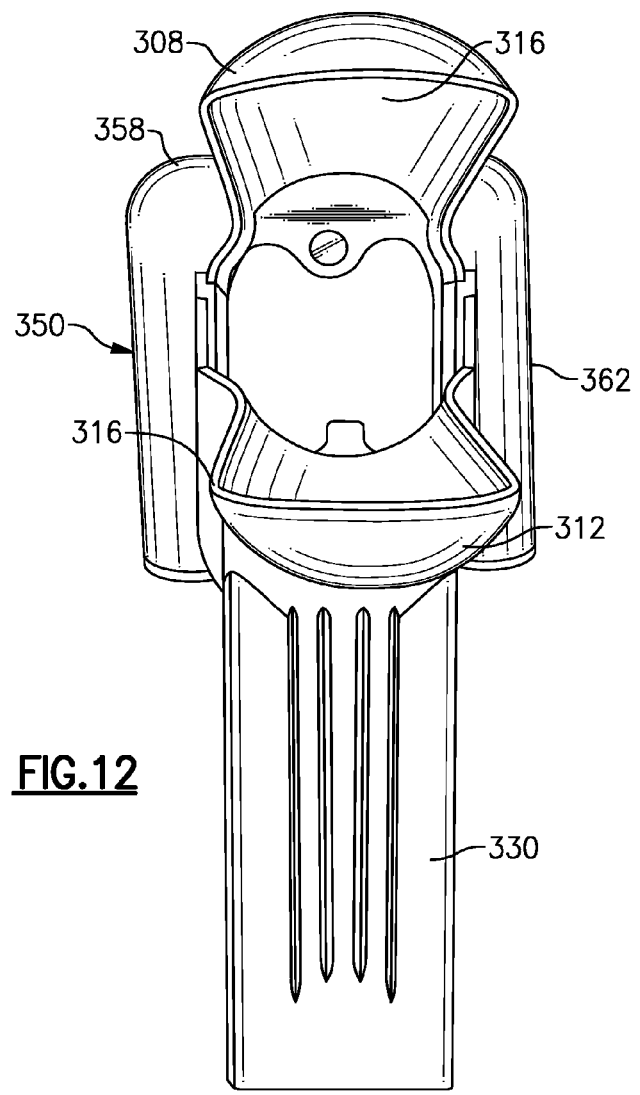
FIG. 12 is a front facing view of the vaginal speculum assembly of FIGS. 10-11.
Figure 13:
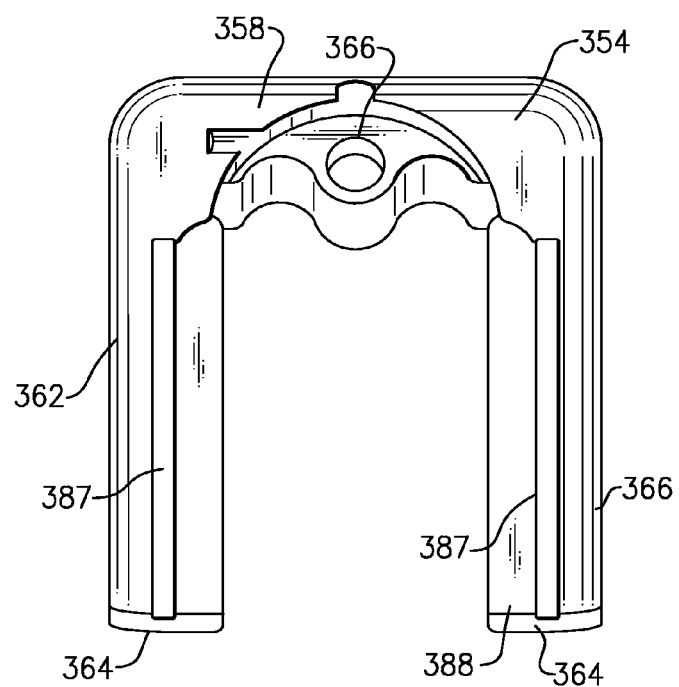
FIG. 13 is a front facing view of the illuminator of the vaginal speculum assembly of FIGS. 10-12.

With reference to FIGS. 7-9, the portable illumination assembly 230 is defined by a housing 236 made from a durable material, such as a moldable plastic, the housing 236 having a lower base portion 260 and a narrower upper portion 245. The upper portion 245 of the housing 236 is sized to entirely fit within the receiving cavity 217 of the handle portion 216 and includes a short tubular portion 238 projecting from a top surface 235 thereof.

Referring to FIG. 7, the upper portion 245 of the housing 236 further includes a set of parallel guide rails 249 (one shown) disposed along opposing sides of the housing 236 that are used to align the illumination assembly 230 with respect to the receiving cavity 217, permitting the housing 236 to be installed in two rotational orientations, 180 degrees spaced from one another.

The interior of the housing 236 is essentially hollow and sized to retain a number of components. As shown in FIG. 9, the tubular projecting portion 238 includes a spacer tube 241. A lens 259 is disposed within the tubular extending portion 238 in a recessed position in which the lens 259 more efficiently couples the output from the contained light source to a light pipe (not shown) of the speculum 204.

An upper portion of the light source is also retained within the spacer tube 241. The light source is a miniature white LED having a domed transparent envelope at its upper end that is aligned with the lens 259 to provide optical coupling therewith. The interior of the spacer tube 241 further provides a surface that acts to direct stray light emitted from the envelope of the LED toward the lens 259.

A lower portion of the LED is retained within a heat sink 244 made from a heat conductive material such as aluminum into which the lower end of the spacer tube 241 extends, as well as the extending electrical contact wires (not shown) from the LED. The heat sink 244 extends substantially across the width of the extending upper portion 245 of the housing 236, with the exception of a recessed portion 272 that accommodates an inner walled cavity 276.

The illumination assembly 230 further retains at least one battery 242, such as a rechargeable lithium ion battery that is disposed within a compartment defined by a pair of tabs 280 configured for retaining the lower end of the battery 242. The upper end of the battery 242 is retained, according to this version, against a portion of an inner wall defining the inner walled cavity 276, the latter being defined to receive a spring-loaded plunger 284 beneath the heat sink 244. The plunger 284 is aligned for movement in a direction that is substantially perpendicular to the primary axis of the illumination assembly 230.

A printed circuit board 240 includes components and circuitry for powering the LED as disposed within the base portion 260 of the assembly housing 236, according to this version. The circuit board 240 includes a feature for controlling the current required to drive the LED, such as a buck-boost constant current LED driver, wherein the circuit board 240 is retained and aligned within the housing 236 using a pair of guide rails 285. A set of spaced charging contacts 286 are disposed immediately beneath the circuit board 240, each of the contacts projecting through a bottom surface 287 of the housing 236. The contained battery 242 is rechargeable, the housing 236 being sized and configured to permit recharging by attachment to a docking station (not shown) using the charging contacts 286. The contacts 286 are spaced to enable the housing 236 to be installed in two 180 degree spaced orientations within the docking station. In one version shown herein, the circuit board 240 further includes a short circuit/over current protection device to prevent shorting and overcharging of the battery 242. A pair of clamping recesses 289, FIG. 8, can be used in conjunction with the charging contacts 286 to allow a "clothespin" mechanism (not shown) to engage therewith for charging or for auxiliary power, if needed.

A conductive strip member 290 extends along an interior side wall of the housing 236, the strip member 290 has a lower end 292 that is disposed adjacent to conductive contacts 243 of the circuit board 240. The conductive strip member 290 extends into the upper extending portion 245 to a set of switch contacts 294 which are disposed on the interior side of a mechanical slider switch 248, the latter being provided on the exterior of the housing 236. The slider switch 248 is configured to permit automatic operation when the illumination housing 236 is placed at least a predetermined distance within the receiving cavity 217. In this version, the spring-loaded plunger 284 is used in conjunction with the interior wall of the receiving cavity 217 to assist in engagement and retaining the illumination assembly 230 within the receiving cavity 217.

The exterior surface of the slider switch 248 includes a pair of external projections 253 that are disposed on each of the upper and lower end of the slider switch 248 to aid in manual operation of the assembly 230. According to this particular version, engagement causes the slide switch 248 to move downwardly against the bias of a coil spring (not shown), biasing the switch 248 in an OFF position, and causing the lower end 292 of the conductive strip member 290 to electrically contact the conductive contacts 243 of the circuit board 240, thereby completing the circuit and causing the LED to energize.

The illumination assembly 230 further permits the slider switch 248 to be manually preset to a locked position, in which the LED can be energized prior to installing the assembly 230 into the receiving cavity 217 of the speculum 204. In this configuration, the slider switch 248 remains in the locked position based on the downward engagement of the switch 248 by finger pressure against one of the external projections 253 that locates a detent pin 261 attached to a leaf spring 263. Finger pressure of the switch 248 enables de-energization of the LED, but no automatic operation when the illumination assembly 230 is locked, irrespective of the position of the housing 236 within the receiving cavity 216.

Otherwise and when not in the "locked" position, removal of the housing 236 from the receiving cavity 217 causes the LED to be automatically de-energized (e.g., by sliding the switch 248 upward to the original position, moving the lower end 292 of the conductive strip member 290 out of contact with the circuit board 240) and thereby de-energizing the contained LED. Further details regarding the illuminator and the above-noted features are described in previously incorporated U.S. Pat. No. 8,435,175 B2.

With the preceding background and now referring to FIGS. 10-13, there is shown a vaginal speculum assembly 300 made in accordance with a first exemplary embodiment, the assembly 300 including a vaginal speculum 304 and a portable illuminator 350. More specifically, the vaginal speculum 304 is made from a durable molded plastic, such as acrylic or polystyrene, and includes an upper blade member 308, a lower blade member 312 and a slide member 377, the latter component having a forked shaped yoke 378 at an upper end thereof. As described herein, the speculum 304 can be disposable, single use or a single patient component. Each of the upper and lower blade members 308, 312 are defined by respective distal and opposing proximal ends 316, 320. A handle portion 330 extends downwardly from the proximal end 316 of the lower blade member 312 and is defined by an open-ended enclosure having a receiving cavity 334. The handle portion 330 according to this embodiment is integrated as part of the lower blade member 312, although alternatively the handle portion 330 could also be provided as a separately attachable component of the overall assembly.

The herein described speculum assembly 300 further includes a moving or articulation mechanism 370 that permits relative movement between the upper and lower blade members 308, 312 in order to dilate a patient (not shown). More specifically, a lever portion 374 downwardly extends from the proximal end 316 of the upper blade member 308 and the slide member 377 extends upwardly from the proximal end 320 of the lower blade member 312. The lever portion 374 is defined by a frame-like structure that includes an opening, defining an aperture to enable viewing of the intended target of interest. Similarly, another aperture is formed by the forked portion of the yoke 378. Each aperture is aligned with one another and through which the user can examine the patient through the upper and lower blade members 308, 312. The lever portion 374 further includes a bottom tab 375.

An intermediate portion of the slide member 377 is movably (axially) disposed within a guide slot 381 extending over the entirety of the length of the rear side of the handle portion 330, the slide member 377 including a lower tongue 383 for engaging a set of teeth 385 provided in the rear side of the handle portion 330, as well as the upper forked section or yoke 378. The yoke 378 further includes a flexible arcuate projection 384 extending outwardly from the proximal end of the speculum 304 and having a spaced set of ratchet teeth 386 defined along the projection 382. More specifically, the ratchet teeth 386 are provided on a bottom surface of the projection 384 and are further configured to engage the bottom tab 375 of the lever portion 374. Finger pressure applied onto the bottom tab 375 allows the user to angularly articulate or move the blade members 308, 312 of the speculum 304 based on engagement of the tab 375 with the ratchet teeth 386. In addition, the slide member 377, including the yoke 378 and extending lower tongue 383, is configured to permit vertical adjustment between the upper and lower blade members 308, 312 based on engagement between the lower tongue 383 and the set of teeth 385 provided along the rear or proximal side of the handle portion 330.

Still referring to FIGS. 10-13 and according to this exemplary embodiment, the illuminator 350 is defined by a housing 354 that includes a base section 358 and a pair of transverse legs 362 extending in parallel from ends of the base section 358 and forming a substantially inverted U-shaped configuration. The base section 358 is further configured and sized to retain at least one LED (not shown) that is disposed in a center portion 366 of the base section 358, while each of the transverse legs 362 are configured and sized according to this exemplary embodiment to retain a battery (not shown), which is electrically connected to the at least one LED. For purposes of this embodiment, each of the transverse legs 362 includes a cap 364 to enable access to the interior for installing and removing the battery. In addition, a switch (not shown) disposed on the exterior of the housing 354 is configured to enable energization and de-energization of the contained LED.

According to this exemplary embodiment, the portable illuminator 350 is configured to be releasably attached to the moving mechanism 370 and more specifically to the lever portion 374 of the speculum 304. In this configuration, each of the transverse legs 362 are spaced in parallel relation along opposing sides of the frame of the lever portion 374 and in which a pair of guide rails 387 are formed on a front facing side 388 of each of the legs 362 enable placement into a predetermined position. More specifically and according to this embodiment, the guide rails 387 form a substantially U-shaped groove with portions of the housing 354 along the transverse legs 362. These grooves are shaped to complement the shape of horizontal projections (not shown) from lateral sides of the frame of the lever portion 374 bordering the defined aperture. Thus, sliding the illuminator 350 into engagement with the lever portion 374 results in the grooves being substantially "filled" by the projections and creating positive engagement between the lever portion 374 and the illuminator 350. The base section 358 is configured upon attachment to position the LED at the proximal end 320 of the upper blade member 308 so as to direct light toward the distal end 316 of the speculum 304 with the transverse legs 362 being disposed along the lateral sides of the lever portion 374, but not sufficiently to block the user apertures which are defined in each of the lever portion 374 and the yoke 378, respectively.

Figure 17:
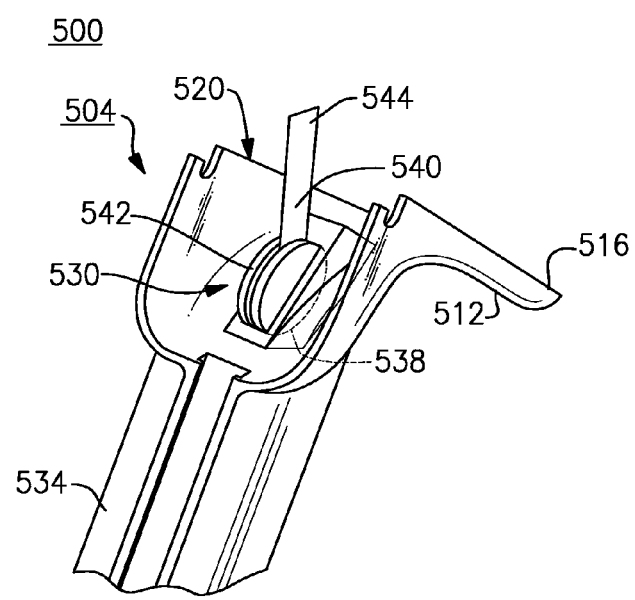
FIG. 17 is a partial rear perspective view of the vaginal speculum assembly of FIG. 16.

The form of the portable illuminator is intended to be exemplary wherein other suitable housing configurations can be suitably configured for attachment to either or both of the lever portion 377 and the yoke 378. Preferably, however, the form of mount should still enable the user to adequately view the intended target of interest through the viewing apertures at the rear of the speculum 304. Additionally and in lieu of a manual switch, such as a slider or other actuable or depressible switch, on the exterior of the housing 354, it will be readily apparent that other suitable versions can be provided for selectively energizing the contained light source (i.e., LED). For example and according to one alternative version, a tab such as 540, FIG. 17, can extend outwardly from the housing 354, one interior end of the tab being connected to switch contacts or otherwise blocking the circuit until removed. An outwardly extending end 544, FIG. 17, of the tab 540 can be pulled by the user to remove the tab 540 from the housing 354, thereby closing the circuit and causing energization of the contained LED.

Figure 19:
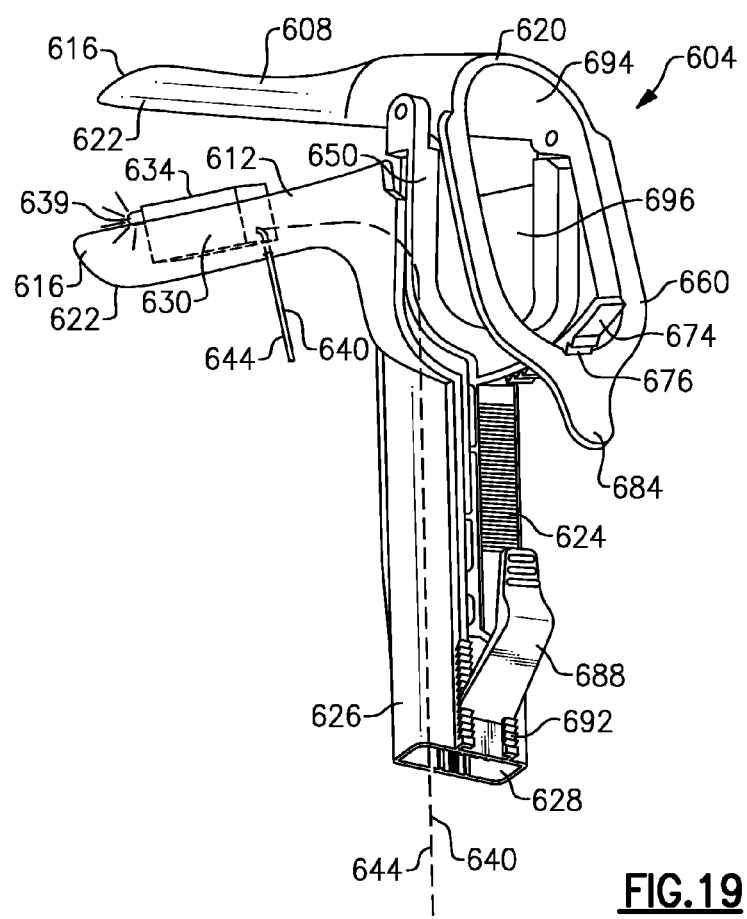
FIG. 19 is a side elevational view of a vaginal speculum assembly made in accordance with another exemplary embodiment.

The extending tab can have a length sufficient to permit access to the housing 354 or can be directed elsewhere, such as through the handle portion 330 for access through the open end thereof or alternatively through at least one slit, slot, opening, cavity or other similar access feature that is provided in the upper blade member 308 and the lower blade member 312, including the handle portion 330. One exemplary version with the latter configuration is also shown in FIG. 19, discussed infra.

Figure 14:
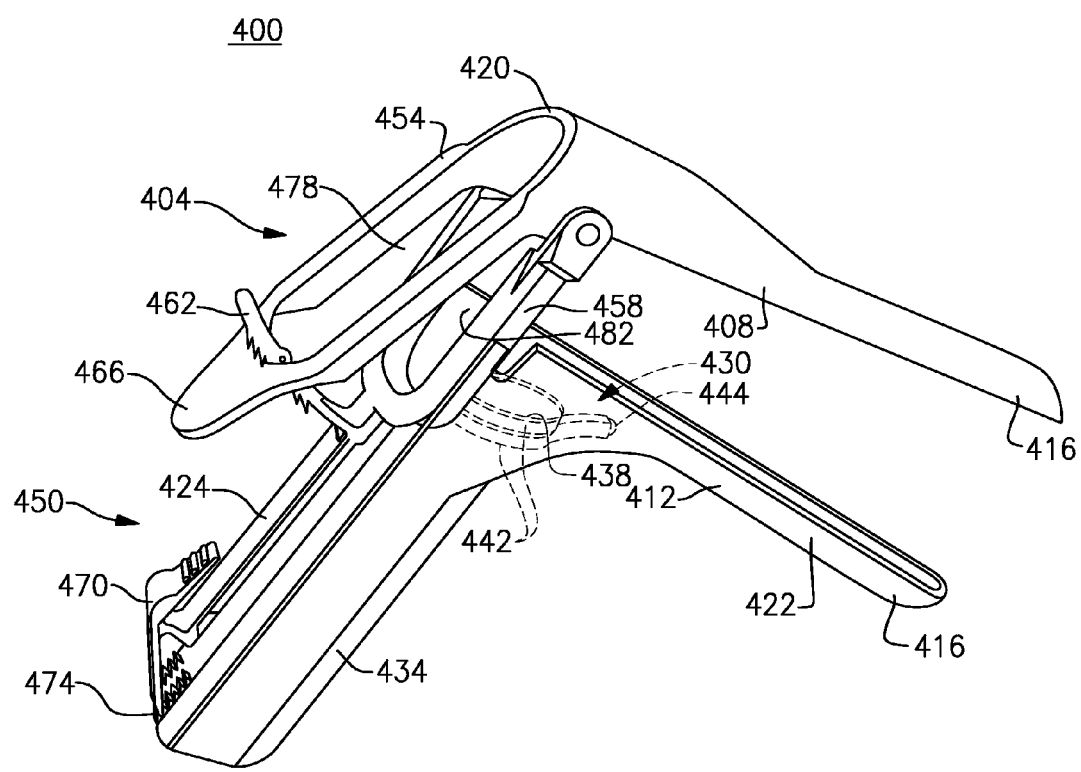
FIG. 14 is a side perspective view of a vaginal speculum assembly in accordance with another exemplary embodiment.
Figure 15:
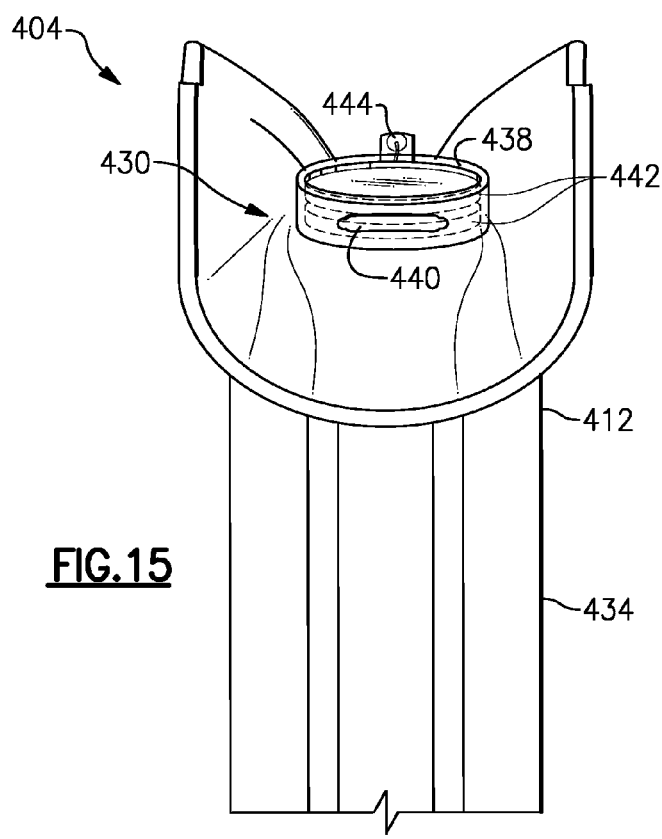
FIG. 15 is a rear facing view of the vaginal speculum assembly of FIG. 14.

Referring to FIGS. 14 and 15, another exemplary version of a vaginal speculum assembly 400 is shown, the assembly 400 including a disposable speculum 404 and a portable illuminator 430. By "disposable", it is intended that the assembly 400 can be discarded following a single use or following a single patient use. Similar to prior embodiments, the disposable speculum 404 is made from a moldable plastic material, such as an acrylic or polystyrene, and includes an upper blade member 408, a lower blade member 412 and a slide member 424 that interconnects the upper and lower blade members 408, 412. Each of the upper and lower blade members 408, 412 are defined by respective distal and proximal ends 416, 420 as well as trough-shaped blade portions 422 and in which the lower blade member 412 further includes a handle portion 434 that downwardly extends from the proximal end 420 that enables the speculum 404 to be maintained using one hand of the user/caregiver.

As in the preceding versions, the speculum 404 according to this exemplary embodiment is further defined by a moving or articulation mechanism 450 that comprises a lever portion or member 454 extending downwardly from the proximal end 420 of the upper blade member 408 and a yoke 458 disposed at the upper end of the slide member 424. An outwardly flexible arcuate projection 462 formed at the lower center of the yoke 458 is disposed to engage a bottom tab 466 of the lever member 466 to provide pivotal adjustment between the upper and lower blade members 408, 412. Though not shown, the flexible arcuate projection 462 can include a series of ratchet teeth that provide the required adjustment. Additionally, the slide member 424 is movable within a guide slot arranged along the rear side of the handle portion 434. A lower tongue 470 of the slide member 424 is configured relative to a set of teeth 474 disposed at the bottom of the handle portion 434 to permit vertical movement of the slide member 424 and yoke 458 relative to the lower blade member 412. Each of the lever portion 454 and the yoke 458 further define respective and aligned openings or viewing apertures 478 and 482 at the proximal end of the speculum 404 to permit viewing of an intended target.

Like the remainder of the lower blade member 412, the handle portion 434 according to this embodiment is also made from a molded plastic material and is configured to enable the speculum 404 to be held and used using a single hand of a caregiver. In addition, the handle portion 434 can be configured to act as a housing for a portable illumination assembly 430. As shown in FIGS. 14 and 15, the upper end of the handle portion 434 is formed or alternatively retains a cylindrical receptacle 438 that is sized and configured to retain a pair of vertically stacked compact batteries 442, as well as an LED 444 that is electrically connected to the batteries 442 through respective contacts (not shown) and suitably positioned from the receptacle 438 in order to permit emitted light to be directed toward the distal end 416 of the speculum 404 and the intended target. For purposes of this exemplary embodiment, the LED 444 may be retained within an extending portion of the receptacle 438 and disposed at a distal end thereof. Alternatively, the LED 444 may simply be connected to the receptacle 438 via contacts extending from the batteries 442 to the LED 444. In this particular version, a light pipe is not required and illumination is made directly to the distal end 416 of the speculum 404. The receptacle 438 can be molded as an integral part of the lower blade member 412 or can be otherwise formed and separately attached using suitable techniques such as bonding, adhesives, welding and the like. According to this exemplary version, the illumination assembly 430 is intended to be disposable along with the speculum 404, with the receptacle 438, batteries 442 and LED 444 being non-releasably retained. Energization of the illumination assembly 430 (LED 444) can be made using various means. According to the depicted version, the receptacle 438 includes a slot 440 that enables the user to access an extending tab (not shown) that is situated between the contained batteries 442 and thereby forms a switch. Removal of the extending tab enables the batteries 442 to make contact with one another to energize the LED 444. In an alternate version, the application of pressure by the user to a predetermined section of the lower blade member 412 or the receptacle 438 can complete the circuit relative to the contained batteries 442 and also cause the contained LED 444 to be energized. In yet another version, a wireless switch within the assembly can be enabled, such as through the transmission of an RF or IR signal. According to at least one other version, an extending tab 540, FIG. 17, can be alternatively provided that extends from a wall of either the handle portion 434 or alternatively though one of the upper and lower blade members 408, 412 using a slit, slot, opening or other access feature.

Figure 16:
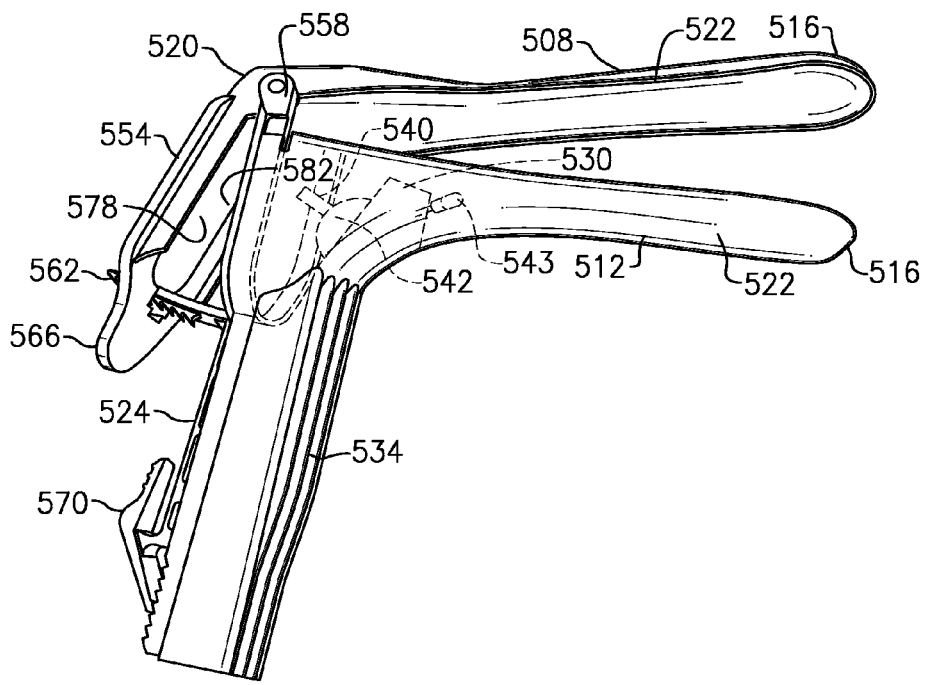
FIG. 16 is a side perspective view of a vaginal speculum assembly in accordance with another exemplary embodiment.

Alternative configurations can be contemplated. For example and according to FIGS. 16 and 17, another vaginal speculum assembly 500 is depicted comprising a disposable plastic speculum 504 and an illumination assembly 530. As in the preceding versions, the disposable speculum 504 is made from a moldable plastic material, such as an acrylic or polystyrene, and includes an upper blade member 508, a lower blade member 512 and a slide member 524 that interconnects the upper and lower blade members 508, 512. Each of the upper and lower blade members 508, 512 are defined by respective distal and proximal ends 516, 520, as well as trough-shaped blade portions 522 and in which the lower blade member 512 further includes a handle portion 534 that downwardly extends from the proximal end 520 that enables the speculum 504 to be maintained using one hand of the user/caregiver.

Also and as in the preceding versions, the speculum 504 is further defined by a moving or articulation mechanism 550 that comprises a lever portion or member 554 extending downwardly from the proximal end 520 of the upper blade member 508 and a yoke 558 disposed at the upper end of the slide member 524. An outwardly flexible arcuate projection 562 is formed at the lower center of the yoke 558 and disposed to engage a bottom tab 566 of the lever member 554 in order to provide pivotal adjustment between the upper and lower blade members 508, 512. Though not shown, the flexible arcuate projection 562 can include a series of ratchet teeth that provide the required adjustment. Additionally, the slide member 524 is movable within a guide slot arranged along the rear side of the handle portion 534. A lower tongue 570 of the slide member 524 is configured relative to a set of teeth (not shown in this view) disposed at the bottom of the handle portion 534 to permit vertical movement of the slide member 524 and yoke 558 relative to the lower blade member 512. In addition, each of the lever portion 554 and the yoke 558 further define respective and aligned openings or viewing apertures 578 and 582 at the proximal end of the speculum 504 to permit viewing of an intended target.

In this specific version, a recess 538 is formed at the upper end of the handle portion 534 that is sized and configured to form a housing or enclosure for the components of the illumination assembly 530. More specifically, a pair of batteries 542 are horizontally stacked in relation to one another within the recess 538 along with an LED 543, such as a white or colored LED, that can optionally be attached to a circuit board or directly connected to the batteries 542. The LED 543 is positioned relative to the defined recess 538 in order to distally direct light along the lower blade member 512 toward the intended target using a light pipe or via direct illumination. An end of an extending tab 540 is tightly disposed between the batteries 542. The extending tab 540 comprises a thin strip-like section of a non-conductive material, such as plastic that is interposed to prevent electrical contact. In one version, the batteries 542 are tightly fitted in the recess 538 a manner that would complete the circuit without the presence of the interposed tab 540. The tab 540 is configured to break the circuit until pulled. The tab 540 includes an extending end portion 544 that enables the tab 540 to be pulled from the illumination assembly 530 and closes the circuit to enable energization of the contained LED. According to this embodiment, the tab 540 is accessible through the rear viewing apertures 578, 582 formed by the lever portion 574 and the yoke 558.

Figure 18:
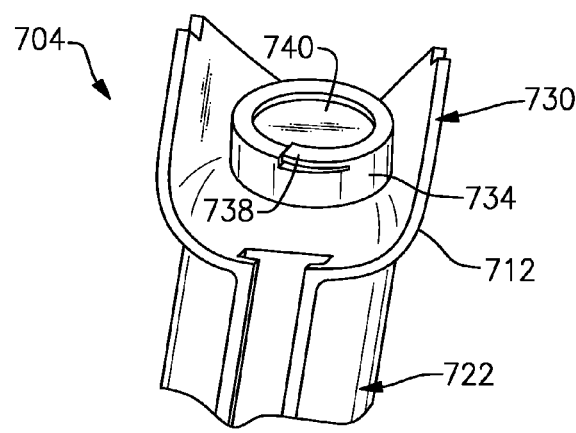
FIG. 18 is a rear facing view of a vaginal speculum assembly made in accordance with another exemplary embodiment.

Another variation of a vaginal speculum assembly 700 that is configured to maintain an illumination assembly 730 is partially depicted in FIG. 18, wherein a molded enclosure 734 is provided or otherwise molded as part of the lower blade member 712 of the speculum 704, the speculum 704 further including a downwardly extending handle portion 722. In this version, a set of batteries 740 are disposed in a stacked configuration within the defined enclosure 734 with contacts (not shown) extending to an LED (not shown) supported in relation to the trough portion of the lower blade member 712. Initially, the batteries 740 are disposed within the enclosure 734 such that a small spacing is created therebetween that prevents contact between the batteries 740. According to this embodiment, a rear or proximal portion of a top surface of the enclosure 734 is formed as a spring-like cantilevered portion that forms a lever 738. The lever 738 is configured to act as a switch to selectively engage the retained batteries 740 when depressed; that is, when the lever 738 is pushed toward the contained batteries 740, causing the batteries 740 to be placed into contact with one another and completing the circuit to energize the LED.

Each of the foregoing arrangements discussed relate to an illuminator assembly disposed at or near the proximal end of a vaginal speculum. However, still other variations can be contemplated. Referring to FIG. 19 and according to another exemplary embodiment, there is provided a vaginal speculum assembly 600, which is also defined by a vaginal speculum 604 and an illumination assembly 630. As in the preceding versions, the vaginal speculum 604 is preferably made from a molded plastic material, such as acrylic or polystyrene, and includes an upper blade member 608 and a lower blade member 612, as well as a slide member 624 that interconnects the upper and lower blade members 608, 612. Each of the upper and lower blade members 608, 612 are further defined by respective opposing distal and proximal ends 616, 620, in which each distal end 616 is further defined by a trough-shaped blade portion 622. A handle portion 626 extends downwardly from the proximal end 620 of the lower blade member 612 to enable one-handed operation. The handle portion 626 according to this version is defined by a receiving cavity extending therethrough, including an open end 628.

Also and as in the preceding versions, the slide member 624 defines part of a moving or articulation mechanism that includes a forked yoke 650 at the upper end of the slide member 624. A lever member or portion 660 extends downwardly from the proximal end of the upper blade member 608. The lever member 660 includes a bottom tab 684 that engages a flexible arcuate projection 674 that is formed at the lower portion of the yoke 650, and more specifically a set of ratchet teeth 676 provided on a downward facing surface of the arcuate projection 674. The engagement between the bottom tab 684 of the lever portion 660 and the ratchet teeth 676 of the flexible arcuate extension 674 enable pivotal adjustment between the upper and lower blade members 608, 612, while the engagement of a lower tongue 688 of the slide member 624 with a set of teeth 692 on the proximal side of the handle portion 626 of the speculum 604 permits vertical adjustment of spacing between the upper and lower blade members 608, 612. In addition, each of the lever portion 660 and the yoke 650 define aligned viewing apertures 694, 696 at the rear of the speculum 604 to enable a user to view the intended target (e.g., cervix).

The portable illuminator assembly 630 is defined by a compact housing 634, shown schematically herein and having a size that permits placement, whether releasably or by mounting or molding within at least a portion of the trough-shaped distal blade portions 622 of one of the upper and lower blade members 608, 612 of the speculum 604. In this depicted version, the illuminator housing 634 is disposed entirely within the trough-shaped distal portion 622 of the lower blade member 612, the housing 634 being configured to retain at least one battery and a light source 639, such as an LED (not shown), within the interior of the housing 634 that is configured to direct light toward the distal end 616 of the speculum 604.

According to this embodiment, a switch comprises an extending tab 640 having an interior end that engages with contacts (not shown) disposed within the housing 634 and an oppositely disposed exterior end 644. The tab 640 is preferably made from a flexible non-conductive material, such as plastic, wherein the first end prevents an electrical connection between the retained LED and battery. Removal of the tab 640 closes the circuit and causes energization of the retained LED.

The lower blade member 612 can include at least one clip, cavity, slot or other retention feature within the trough shaped distal portion 622 to permit the releasable attachment of the illumination assembly 630. Alternatively, the illumination assembly 630 can be molded integrally within the lower blade portion 612. In terms of positioning, the illumination assembly 630 can be fully disposed within the trough-shaped blade portion 622, as depicted herein or the illumination assembly 630 can be at least partially situated within the blade portion 622 and extend toward the proximal end of the speculum 604.

In terms of operation, the light source 639 of the illumination assembly 630 can be energized by pulling an extending end of the tab 640 through a slot, slit, opening or other access feature 648 provided in the lower blade member 612, thereby closing the circuit or alternatively by extending the tab through the handle portion. Alternatively, the extending tab 640 can be directed such the extending end is accessible from the open end 628 of the handle portion 626. Light emitted by the light source 639 is directly transmitted to the intended target through the distal opening formed between the upper and lower blade members 608, 612 enabling the target to be viewed without interference through the defined rear viewing apertures 694, 696 of the speculum 604.

Various modifications are possible in terms of the foregoing embodiments. For example, other forms of switches can be used in lieu of the extending tab 640. For example, the housing can include an exterior switch accessible to the user, either through a slot or other access feature that is formed in the lower blade member 612. According to another variant, the illumination assembly 630 can be configured to automatically energize the contained LED upon assembly or include an interiorly disposed wireless switch that can be enabled, for example, by a transmitted RF, IR or other signal without direct physical contact. In addition for the version described according to FIG. 19, the extending tab 640 can be separately disposed for access by the caregiver. For example, the extending tab 640 can be accessed through at least one slot, slit, opening or other access feature formed on either of the upper and lower blade members 608, 612, the walls of the handle portion 626 or the open end 628 of the handle portion 626, the latter being alternatively shown in FIG. 19.

PARTS LIST FOR FIGS. 1-19

100 vaginal speculum assembly
102 speculum, disposable
104 bottom or lower blade member
108 upper or top blade member
112 slide member
120 handle portion
123 flexible rear-extending arcuate projection
124 yoke
125 ratchet teeth
128 lever portion
129 lower tongue
130 single ratchet tooth
131 corresponding teeth
133 receiving cavity
135 opening
137 tab
139 interior slot 140 reusable illumination assembly
144 housing
146 light pipe
147 distal light emitting end
148 distal portion, housing
152 strain relief
156 cable, electrical
160 in-line assembly
163 depressible button
168 pronged plug
172 female plug
174 cable
176 power supply transformer
200 vaginal speculum apparatus or assembly
204 speculum, disposable
208 upper or top blade member
214 lower or bottom blade member
215 elongate trough shaped blade section
216 handle portion
217 receiving cavity
220 slide member
221 proximal end, upper blade member
222 external teeth
223 guide slot
224 lever member or portion
225 flexible projection (arcuate)
226 engagement teeth
227 bottom tab, lever portion
228 yoke
229 lower tongue
230 illuminator
235 top surface
236 illuminator housing
238 tubular projecting portion
240 circuit board
241 spacer tube
242 battery
243 conductive contacts
244 heat sink
245 upper portion, housing
248 slider switch
249 guide rails
250 rail-like portions
253 projections, external
259 lens, collecting
260 base portion
261 detent pin
260 base portion
263 leaf spring
272 recessed portion
276 inner walled cavity
280 tabs
284 plunger, spring loaded
285 guide rails
286 contacts, charging
287 bottom surface
289 clamping recess
290 conductive strip member
292 lower end, conductive strip member
294 switch contacts
299 pins
300 vaginal speculum assembly
304 vaginal speculum
308 upper blade member
312 lower blade member
316 distal end
320 proximal end
322 trough-shaped distal blade portions
330 handle portion
334 receiving cavity
350 portable illuminator
354 housing, illuminator
358 base portion
362 transverse legs
364 cap(s)
366 center portion
370 moving or articulation mechanism
374 lever portion or member
375 bottom tab, lever portion
377 slide member
378 yoke
381 guide slot
383 tongue, lower
384 flexible arcuate projection
385 teeth
386 teeth, ratchet
387 guide rails
388 front facing side, housing
400 vaginal speculum assembly
404 vaginal speculum
408 upper blade member
412 lower blade member
416 distal end
420 proximal end
422 trough-shaped blade portion
424 slide member
430 illumination assembly
434 handle portion
438 receptacle
440 slot, receptacle
442 batteries
444 LED
450 moving or articulation mechanism
454 lever portion or member
458 yoke
462 flexible arcuate projection
466 bottom tab, lever portion
470 lower tongue
474 teeth
478 opening (viewing aperture)
482 opening (viewing aperture)
500 vaginal speculum assembly
504 vaginal speculum
508 upper blade member
512 lower blade member
516 distal end
520 proximal end
522 trough-shaped blade portion
524 slide member
530 illumination assembly
534 handle portion
538 recess
540 tab
542 batteries
543 LED
544 extending end, tab
550 moving or articulation mechanism
554 lever portion or member
558 yoke
562 flexible arcuate projection
566 bottom tab, lever portion
570 lower tongue
578 opening (viewing aperture)
582 opening (viewing aperture)

600 vaginal speculum assembly
604 speculum
608 upper blade member
612 lower blade member
616 distal end
620 proximal end
622 trough-shaped blade portion
624 slide member
626 handle portion
628 open end, receiving cavity
630 illumination assembly
634 housing
639 light source
640 extending tab
644 end, tab
648 access feature
650 yoke
660 lever portion
674 flexible arcuate projection
676 ratchet teeth
684 bottom tab, lever portion
688 lower tongue
692 teeth
694 opening (rear aperture)
696 opening (rear aperture)
700 vaginal speculum assembly
704 speculum
712 lower blade member
722 handle portion
730 illumination assembly
734 molded enclosure
738 lever
740 batteries The preceding description is based on certain exemplary embodiments. It will be readily apparent that other modifications and variations are possible within the intended ambits of this invention, including the following claims. For example, each of the specula used in connection with this description relate to an articulation mechanism according to a specific design. The herein described concepts are equally applicable to other suitable mechanisms that are configured in order to selectively open and close the upper and lower blade members of the speculum.

We claim:

1. A speculum comprising:
a first blade member;
a second blade member, each of the first and second blade members having a distal end and an opposing proximal end;
a moving mechanism interconnecting the first and second blade members and configured for moving the first and second blade members in relation to one another; and
a portable illuminator attached to the moving mechanism, wherein the portable illuminator comprises a housing having a main portion and a pair of legs extending from opposing sides of the main portion, the main portion retaining a light source and in which each of the pair of legs includes a guide rail configured for slidably and releasably mounting the portable illuminator to the speculum wherein the moving mechanism comprises a lever portion extending from the proximal end of the first blade member and a yoke attached to the proximal end of the second blade member, each of the lever portion and yoke being connected to one another and defining a viewing aperture, and in which the pair of legs are mounted to one of the lever portion or yoke in spaced and parallel relation to one another about the viewing aperture.

2. The speculum of claim 1, wherein the portable illuminator is releasably attached to the moving mechanism.

3. The speculum of claim 1, wherein the viewing aperture enables access to a spacing between the distal ends of the first and second blade members and in which the portable illuminator is configured to direct light through the viewing aperture(s).

4. The speculum of claim 1, wherein the portable illuminator comprises a housing containing at least one battery and a light source.

5. The speculum of claim 4, wherein the portable illuminator includes a switch for selectively energizing and deenergizing the contained light source.

6. The speculum of claim 5, wherein the switch comprises an extending tab portion that can be accessed in order to energize the contained light source.

7. The speculum of claim 6, further including a handle portion downwardly extending from the proximal end of the second blade member wherein the handle portion includes a distal end and a proximal end, the extending tab portion being accessible through the proximal end of the handle portion.

8. The speculum of claim 7, wherein the extending tab portion extends through a lateral wall of the handle portion through at least one defined slit.

9. The speculum of claim 1, wherein the housing of the portable illuminator is attached to one of the lever portion and the yoke.

10. The speculum of claim 1, in which the guide rails define grooves that are configured to engage projections formed on lateral sides of the lever portion bordering the defined viewing aperture.

* * * * *